United States Patent
Masaki et al.

[11] Patent Number: 4,962,096
[45] Date of Patent: Oct. 9, 1990

[54] HETEROCYCLIC GLYCEROL DERIVATIVES AND THEIR USE AS ANTI-HYPERTENSIVE AGENTS

[75] Inventors: Mitsuo Masaki, Chiba; Hiromitsu Takeda, Washimiya; Toshiro Kamishiro; Masao Yamamoto, both of Misato, all of Japan

[73] Assignee: Nippon Chemiphar Co., Ltd., Tokyo, Japan

[21] Appl. No.: 172,581

[22] Filed: Mar. 24, 1988

[30] Foreign Application Priority Data

Mar. 24, 1987 [JP] Japan .................. 62-69943
Mar. 24, 1987 [JP] Japan .................. 62-69944
Mar. 31, 1987 [JP] Japan .................. 62-80705
Mar. 31, 1987 [JP] Japan .................. 62-80706

[51] Int. Cl.$^5$ ............... C07F 9/6539; C07F 9/6541; A61K 31/425
[52] U.S. Cl. ........................ 514/92; 514/89; 514/95; 514/96; 546/22; 548/112; 548/113
[58] Field of Search ............ 546/23; 514/89, 92, 514/95, 96; 548/112, 113

[56] References Cited

U.S. PATENT DOCUMENTS

| | | | |
|---|---|---|---|
| 4,408,052 | 10/1983 | Hozumi et al. | 546/22 |
| 4,426,525 | 1/1984 | Hozumi et al. | 546/22 |
| 4,649,203 | 3/1987 | Nojima et al. | 548/112 |
| 4,650,791 | 3/1987 | Nomura et al. | 514/82 |
| 4,710,579 | 12/1987 | Nojima et al. | 558/169 |
| 4,900,731 | 2/1990 | Wissner et al. | 514/77 |

*Primary Examiner*—Alan L. Rotman
*Attorney, Agent, or Firm*—Sixbey, Friedman, Leedom & Ferguson

[57] ABSTRACT

A novel glycerol derivative which is effective to reduce blood pressure has the formula:

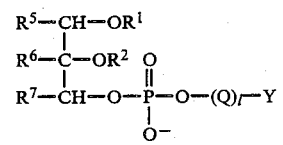

wherein $R^1$ is an alkyl group having 10–22 carbon atoms, $R^2$ is lower acyl, benzoyl, aryl, mono-, di- or triarylalkyl, alkyl, cycloalkyl, or cycloalkylalkyl; Q is substituted or unsubstituted alkylene containing 1–4 carbon atoms, l is 0 or 1; Y is a nitrogen-containing heterocyclic group or a nitrogen-containing bridged heterocyclic group (—(Q)$_l$— is attached to a carbon atom contained in a hetero-ring of the heterocyclic group) in which Y is the bridged heterocyclic group where l is 0; and each of $R^5$, $R^6$ and $R^7$ is hydrogen, lower alkyl, aryl or aralkyl.

7 Claims, No Drawings

HETEROCYCLIC GLYCEROL DERIVATIVES AND THEIR USE AS ANTI-HYPERTENSIVE AGENTS

BACKGROUND OF THE INVENTION

1. Field of the Invention

The present invention relates to a novel glycerol derivative, a process for the preparation of the same and an anti-hypertensive agent containing the glycerol derivative.

2. Description of Prior Art

Recently, studies of a platelet activating factor (PAF) have been advanced, and its physiological function has been made clear. According to the studies, in living body, PAF shows functions relating to allergy, inflammation, and platelet aggregation, and also PAF shows strong blood pressure reducing action (Nature, vol. 285, 193(1980), and European Journal of Pharmacology, 65, 185–192(1980)).

Therefore, studies have been further made for utilizing the excellent blood pressure reducing action of PAF with removal of its unfavorable effects such as platelet aggregating action.

As compounds functioning as PAF, there are known certain glycerol derivatives. Accordingly, extensive studies have been made for discovering new glycerol derivatives having the improved action.

SUMMARY OF THE INVENTION

Accordingly, the present invention has an object to provide a new glycerol derivative which shows a prominent blood pressure reducing action with reduced unfavorable actions such as reduced platelet aggregating action and to provide a process for the preparation of the glycerol derivative.

The invention has a further object to provide an anti-hypertensive agent utilizing the above-mentioned new glycerol derivative.

There is provided by the present invention a novel glycerol derivative having the formula (I):

$$\begin{array}{l} R^5-CH-OR^1 \\ \phantom{R^5-C}| \\ R^6-C-OR^2 \\ \phantom{R^5-C}| \\ R^7-CH-O-\underset{\underset{O^-}{|}}{\overset{\overset{O}{\|}}{P}}-O-(Q)_l-Y \end{array} \quad (I)$$

wherein $R^1$ is a straight or branched chain alkyl group having 10–22 carbon atoms;

$R^2$ is a straight or branched chain acyl group having 1–6 carbon atoms, a benzoyl group which may have one or more substituents, an aryl group which may have one or more substituents, a monoarylalkyl group which may have one or more substituents and which has an alkylene chain having 1–3 carbon atoms, a diarylalkyl group which may have one or more substituents and which has an alkylene chain having 1–3 carbon atoms, a triarylalkyl group which may have one or more substituents and which has an alkylene chain having 1–3 carbon atoms, a straight or branched chain alkyl group having 1–10 carbon atoms, a cycloalkyl group which may have one or more substituents, or a cycloalkylalkyl group which may have one or more substituents and which has an alkylene chain having 1–3 carbon atoms;

Q is a saturated or unsaturated alkylene group which may have one or two alkyl or aryl substituents, said alkylene having 1–4 carbon atoms;

$l$ is 0 or 1;

Y is a nitrogen-containing heterocyclic group which contains as a ring member a group having a formula:

$$-\overset{R^3}{\underset{}{\overset{}{\diagdown}}}\overset{}{\underset{+N-}{}}\overset{R^4}{\underset{}{\diagup}}- \quad \text{or} \quad -\overset{R^3}{\underset{+N=}{|}}$$

wherein each of $R^3$ and $R^4$ independetly is a straight or branched chain alkyl group having 1–6 carbon atoms, or a nitrogen-containing bridged heterocyclic group which contains as a ring member a group having a formula:

$$-\overset{R^3}{\underset{}{\overset{}{\diagdown}}}\overset{}{\underset{+N-}{}}\overset{R^4}{\underset{}{\diagup}}- \quad \text{or} \quad -\overset{R^3}{\underset{+N-}{|}}\diagdown$$

wherein each of $R^3$ and $R^4$ independently has the same meaning as above, wherein said heterocyclic group and bridged heterocyclic group may have at least one substituent group and the group $-(Q)_l-$ is attached to a carbon atom contained in a hetero-ring of the heterocyclic group; and where $l$ is 0, Y is the nitrogen-containing bridged heterocyclic group, and each of $R^5$, $R^6$ and $R^7$ independently is hydrogen, a straight or branched chain alkyl group having 1–6 carbon atoms, an aryl group or an aralkyl group.

The glycerol compound having the formula (I) in which $R^2$ is an acyl or benzoyl can be prepared by a process which comprises acylating a compound having a formula (II):

$$\begin{array}{l} R^5-CH-OR^1 \\ \phantom{R^5-C}| \\ R^6-C-OH \\ \phantom{R^5-C}| \\ R^7-CH-O-\underset{\underset{O^-}{|}}{\overset{\overset{O}{\|}}{P}}-O-(Q)_l-Y \end{array} \quad (II)$$

wherein each of $R^1$, $R^5$, $R^6$ and $R^7$ independently has the same meaning as above, and each of Q, $l$ and Y has the same meaning as above, with an acylating agent containing the group $R^2$ that is a straight or branched chain acyl group having 1–6 carbon atoms or benzoyl.

The glycerol compound having the formula (I) can be also prepared by a process which comprises reacting a compound having the formula (X):

$$\begin{array}{l} R^5-CH-OR^1 \\ \phantom{R^5-C}| \\ R^6-C-OR^2 \\ \phantom{R^5-C}| \\ R^7-CH-OH \end{array} \quad (X)$$

wherein each of $R^1$, $R^2$, $R^5$, $R^6$ and $R^7$ independently has the same meaning as above, with phosphorus oxychloride (i.e., phosphoryl chloride) and a compournd having the formula (V):

$$H-O-(Q)_l-Y.A^- \quad (V)$$

wherein A⁻ is an anion and each of Q, l and Y has the same meaning as above, in the presence of a base.

DETAILED DESCRIPTION OF THE INVENTION

In the formula (I), $R^1$ represents a straight or branched chain alkyl group having 10-22 carbon atoms such as decyl, undecyl, dodecyl, tridecyl, tetradecyl, pentadecyl, hexadecyl, heptadecyl, octadecyl, nonadecyl, eicosyl, heneicosyl or docosyl. $R^1$ preferably is a straight or branched chain alkyl having 12-20 carbon atoms.

$R^2$ represents a straight or branched chain acyl having 1-6 carbon atoms such as formyl, acetyl, propionyl, butyryl, isobutyryl, valeryl, isovaleryl or pivaloyl, or a benzoyl group which may have one or more substituetns. Otherwise, $R^2$ is an aryl group (e.g., phenyl or naphthyl) which may have one or more substituents, a monoarylalkyl group which may have one or more substituents and which has an alkylene chain having 1-3 carbon atoms (e.g., benzyl or phenylethyl), a diarylalkyl group which may have one or more substituents and which has an alkylene chain having 1-3 carbon atoms (e.g., benzhydryl), a triarylalkyl group which may have one or more substituents and which has an alkylene chain having 1-3 carbon atoms (e.g., trityl), a straight or branched chain alkyl group having 1-10 carbon atoms (e.g., methyl, ethyl, propyl, butyl, pentyl, hexyl, heptyl, octyl, 2-ethylhexyl, nonyl, or decyl), a cycloalkyl group (e.g., cyclopentyl, cyclohexyl or cycloheptyl) which may have one or more substituents, or a cycloalkylalkyl group (e.g., cyclohexylmethyl or cyclohexylethyl) which may have one or more substituents and which has a non-cyclic alkylene chain having 1-3 carbon atoms. The substitutents may be a lower alkyl group having 1-6 carbon atoms or a lower alkoxy group having 1-6 carbon atoms. $R^2$ preferably is a straight chain acyl group having 2-6 carbon atoms.

$R^5$, $R^6$ and $R^7$ are the same as or different from each other, and each independently represents hydrogen or a straight or branched chain alkyl group having 1-6 carbon atoms such as methyl, ethyl, n-propyl, isopropyl, n-butyl, isobutyl, pentyl or hexyl, an aryl group such as phenyl or a substituted phenyl (e.g., tolyl or xylyl), or an aralkyl group preferably having an alkylene bonding of 1-3 carbon atoms such as benzyl or phenylethyl. In preferred embodiments, (1) $R^5$, $R^6$ and $R^7$ are all hydrogens, (2) $R^5$ is a straight or branched chain alkyl group having 1-6 carbon atoms and $R^6$ and $R^7$ are both hydrogens, and (3) $R^7$ is a straight or branched chain alkyl group having 1-6 carbon atoms and $R^5$ and $R^6$ are both hydrogens.

Q is a saturated or unsaturated alkylene group (said alkylene contains 1-4 carbon atoms) which may have one or two alkyl groups (preferably a lower alkyl group of 1-4 carbon atoms) or aryl group (preferably phenyl) as substitutent group(s), and l is 0 or 1.

Y is a nitrogen-containing heterocyclic group or a nitrogen-containing bridged heterocyclic group. The nitrogen-containing heterocyclic group contains as a ring member a group having a formula:

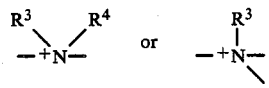

and the nitrogen-containing bridged heterocyclic group contains as a ring member a group having a formula:

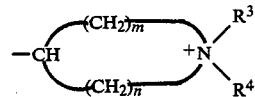

The heterocyclic group and bridged heterocyclic group may have one more substituents such as an alkyl having 1-6 carbon atoms, an aryl group such as phenyl, an aromatic ring which is fused with the heterocyclic group. The hetercyclic group and bridged heterocyclic group may have other hetero atoms such as sulfur atom and oxygen atom, and can be a saturated or unsaturated heterocyclic group.

$R^3$ and $R^4$ are the same as or different from each other, and each independently represents a straight or branched chain alkyl group having 1-6 carbon atoms such as methyl, ethyl, n-propyl, isopropyl, n-butyl, isobutyl, pentyl or hexyl.

In the formula (I), the group -(Q)$_l$- is attached to a carbon atom contained in a hetero-ring of the heterocyclic group.

In one aspect, a preferred glycerol derivative has the formula (I) wherein l is 1 and Y has a nitrogen-containing heterocyclic group having the formula:

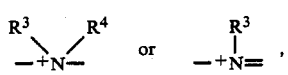

wherein each of $R^3$ and $R^4$ independently has the same meaning as above, and each of m and n independently is 0 or a positive integer under the condition of m+n=2-8 (preferably m+n=3-5).

Examples of ring structures of the nitrogen-containing heterocyclic groups having the above formula include the following groups wherein the substitutent groups of $R^3$ and $R^4$ are omitted: 2-pyrrolidinyl, 3-pyrrolidinyl, 2-piperidinyl, 3-piperidinyl, 4-piperidinyl, 2-perhydroazepinyl, and 3-perhydroazepinyl.

Examples of the heterocyclic groups include quaternary ammonium salts of pyrrolidinyl, piperidinyl, morpholinyl, perhydroazepinyl, pyrrolyl, oxazolyl, imidazolyl, quinolinyl, tetrahydroquinolinyl, isoquinolinyl, tetrahydroisoquinolinyl, thiazolidinyl, oxazolidinyl, thiazolyl, pyridyl, tetrahydropyridyl, benzothiazolyl, benzoxazolyl, tetrazolyl, triazolyl, and benzimidazolyl.

Examples of ring structures of the nitrogen-containing bridged heterocyclic groups include the following groups wherein the substitutent groups of $R^3$ and $R^4$ are omitted: 2-azoniabicyclo[2,2,1]-3-heptyl; 2-azoniabicyclo[2,2,1]-5-heptyl; 2-azoniabicyclo[2,2,1]-6-heptyl; 2-azoniabicyclo[2,2,2]-3-octyl; 2-azoniabicyclo[2,2,2]-5-octyl; 2-azoniabicyclo[2,2,2]-6-octyl; 3-azoniabicyclo[3,2,1]-6-octyl; 3-azoniabicyclo[3,2,1]-8-octyl; 8-azoniabicyclo[3,2,1]-3-octyl; 8-azoniabicyclo[3,2,1]-2-octyl; 8-azoniabicyclo[3,2,1]-6-octyl; 8-azoniabicyclo[4,3,1]-10-decyl; 2-azoniabicyclo[3,3,1]-9-nonyl; 9-azoniabicyclo[3,3,1]-3-nonyl; 9-azoniabicyclo[4,2,1]-2-nonyl; 2-azoniabicyclo[4,3,1]-10-decyl; 2-azoniabicyclo[4,4,0]-4-decyl; 8-azoniabicyclo[4,3,1]-10-decyl; 1-azoniabicyclo[2,2,1]-2-heptyl; 1-azoniabicyclo[2,2,1]-3-heptyl; 1-azoniabicyclo[2,2,1]-7-heptyl; 1-azoniabicyclo[2,2,2]-2-octyl; 1-azoniabicyclo[2,2,2]-3-octyl; 1-azoniabicyclo[2,2,2]-4-octyl; 1-azoniabicyclo[3,2,1]-3-octyl; 1-azoniabicyclo[3,2,1]-4-octyl; 1-azoniabicyclo[3,2,1]-6-heptyl; 1-azoniabicyclo[4,2,0]-2-octyl; 1-azoniabicyclo[4,2,0]-7-octyl; 1-azoniabicyclo[4,3,0]-5-nonyl; 1-azoniabicyclo[4,3,0]-7-noyl; 1-azoniabicyclo[4,3,1]-3-decyl; 1-azoniabicyclo[4,4,0]-2-decyl; and 1-azoniabicyclo[4,4,0]-5-decyl.

Examples of the glycerol derivatives having the formula (I) are as follows:

(1) 2-acetyloxy-3-hexadecyloxypropyl 1,1-dimethylpiperidinio-3-ylmethyl phosphate;
(2) 2-acetyloxy-3-hexadecyloxypropyl 1,1-diethylpiperidinio-3-ylmethyl phosphate;
(3) 3-hexadecyloxy-2-propionyloxypropyl 1,1-dimethylpiperidinio-3-ylmethyl phosphate;
(4) 2-benzoyloxy-3-hexadecyloxypropyl 1,1-dimethylpiperidinio-3-ylmethyl phosphate;
(5) 2-acetyloxy-3-octadecyloxypropyl 1,1-dimethylpiperidinio-3-ylmethyl phosphate;
(6) 2-acetyloxy-3-hexadecyloxybutyl 1,1-dimethylpiperidinio-3-ylmethyl phosphate;
(7) 2-acetyloxy-3-hexadecyloxy-1-methylpropyl 1,1-dimethylpiperidinio-3-ylmethyl phosphate;
(8) 2-acetyloxy-3-hexadecyloxypropyl 1-(1,1-dimethylpiperidinio-3-yl)ethyl phosphate;
(9) 2-acetyloxy-3-hexadecyloxypropyl 2-(1,1-dimethylpiperidinio-3-yl)ethyl phosphate;
(10) 2-acetyloxy-3-hexadecyloxypropyl 1,1-dimethylpiperidinio-2-ylmethyl phosphate;
(11) 2-acetyloxy-3-hexadecyloxypropyl 1,1-diethylpiperidinio-2-ylmethyl phosphate;
(12) 3-hexadecyloxy-2-propionyloxypropyl 1,1-dimethylpiperidinio-2-ylmethyl phosphate;
(13) 2-benzoyloxy-3-hexadecyloxypropyl 1,1-dimethylpiperidinio-2-ylmethyl phosphate;
(14) 2-acetyloxy-3-octadecyloxypropyl 1,1-dimethylpiperidinio-2-ylmethyl phosphate;
(15) 2-acetyloxy-3-hexadecyloxybutyl 1,1-dimethylpiperidinio-2-ylmethyl phosphate;
(16) 2-acetyloxy-3-hexadecyloxy-1-methylpropyl 1,1-dimethylpiperidinio-2-ylmethyl phosphate;
(17) 2-acetyloxy-3-hexadecyloxypropyl 1-(1,1-dimethylpiperidinio-2-yl)ethyl phosphate;
(18) 2-acetyloxy-3-hexadecyloxypropyl 2-(1,1-dimethylpiperidinio-2-yl)ethyl phosphate;
(19) 2-acetyloxy-3-hexadecyloxypropyl 1,1-dimethylpiperidinio-4-ylmethyl phosphate;
(20) 3-hexadecyloxy-2-propionyloxypropyl 1,1-dimethylpiperidinio-4-ylmethyl phosphate;
(21) 2-acetyloxy-3-octadecyloxypropyl 1,1-dimethylpiperidinio-4-ylmethyl phosphate;
(22) 2-acetyloxy-3-hexadecyloxybutyl 1,1-dimethylpiperidinio-4-ylmethyl phosphate;
(23) 2-acetyloxy-3-hexadecyloxy-1-methylpropyl 1,1-dimethylpiperidinio-4-yl phosphate;
(24) 2-acetyloxy-3-hexadecyloxypropyl 2-(1,1-dimethylpiperidinio-4-yl)ethyl phosphate;
(25) 2-acetyloxy-3-hexadecyloxypropyl 1,1-dimethylpyrrolidinio-2-ylmethyl phosphate;
(26) 2-acetyloxy-3-hexadecyloxypropyl 1,1-diethylpyrrolidinio-2-ylmethyl phosphate;
(27) 3-hexadecyloxy-2-propionyloxypropyl 1,1-dimethylpyrrolidinio-2-ylmethyl phosphate;
(28) 2-benzoyloxy-3-hexadecyloxypropyl 1,1-dimethylpyrrolidinio-2-ylmethyl phosphate;
(29) 2-acetyloxy-3-octadecyloxypropyl 1,1-dimethylpyrrolidinio-2-ylmethyl phosphate;
(30) 2-acetyloxy-3-hexadecyloxybutyl 1,1-dimethylpyrrolidinio-2-ylmethyl phosphate;
(31) 2-acetyloxy-3-hexadecyloxy-1-methylpropyl 1,1-dimethylpyrrolidinio-2-ylmethyl phosphate;
(32) 2-acetyloxy-3-hexadecyloxypropyl 1-(1,1-dimethylpyrrolidinio-2-yl)ethyl phosphate;
(33) 2-acetyloxy-3-hexadecyloxypropyl 2-(1,1-dimethylpyrrolidinio-2-yl)ethyl phosphate;
(34) 2-acetyloxy-3-hexadecyloxypropyl 1,1-dimethylpyrrolidinio-3-ylmethyl phosphate;
(35) 2-acetyloxy-3-hexadecyloxypropyl 1,1-diethylpyrrolidinio-3-ylmethyl phosphate;
(36) 3-hexadecyloxy-2-propionyloxypropyl 1,1-dimethylpyrrolidinio-3-ylmethyl phosphate;
(37) 2-benzoyloxy-3-hexadecyloxypropyl 1,1-dimethylpyrrolidinio-3-ylmethyl phosphate;
(38) 2-acetyloxy-3-octadecyloxypropyl 1,1-dimethylpyrrolidinio-3-ylmethyl phosphate;
(39) 2-acetyloxy-3-hexadecyloxybutyl 1,1-dimethylpyrrolidinio-3-ylmethyl phosphate;
(40) 2-acetyloxy-3-hexadecyloxy-1-methylpropyl 1,1-dimethylpyrrolidinio-3-ylmethyl phosphate;
(41) 2-acetyloxy-3-hexadecyloxypropyl 1-(1,1-dimethylpyrrolidinio-3-yl)ethyl phosphate;
(42) 2-acetyloxy-3-hexadecyloxypropyl 2-(1,1-dimethylpyrrolidinio-3-yl)ethyl phosphate;
(43) 2-acetyloxy-3-hexadecyloxypropyl 1,1-dimethylperhydroazepinio-2-ylmethyl phosphate;
(44) 2-acetyloxy-3-hexadecyloxypropyl 1,1-dimethylperhydroazepinio-3-ylmethyl phosphate;
(45) 2-acetyloxy-3-hexadecyloxypropyl 8,8-dimethyl-8-azoniabicyclo[3,2,1]-3-octylmethyl phosphate;
(46) 2-acetyloxy-3-octadecyloxypropyl 8,8-dimethyl-8-azoniabicyclo[3,2,1]-3-octylmethyl phosphate;
(47) 3-hexadecyloxy-2-propionyloxyproyl 8,8-dimethyl-8-azoniabicyclo[3,2,1]-3-octylmethyl phosphate;
(48) 2-acetyloxy-3-hexadecyloxybutyl 8,8-dimethyl-8-azoniabicyclo[3,2,1]-3-octylmethyl phosphate;
(49) 2-acetyloxy-3-hexadecyloxypropyl 1-methyl-1-azoniabicyclo[2,2,2]-3-octylmethyl phosphate;
(50) 2-acetyloxy-3-octadecyloxypropyl 1-methyl-1-azoniabicyclo[2,2,2]-3-octylmethyl phosphate;
(51) 3-hexadecyloxy-2-propionyloxypropyl 1-methyl-1-azoniabicyclo[2,2,2]-3-octylmethyl phosphate;
(52) 2-acetyloxy-3-hexadecyloxybutyl 1-methyl-1-azoniabicyclo[2,2,2]-3-octylmethyl phosphate;
(53) 2-acetyloxy-3-hexadecyloxypropyl 1-methyl-1-azoniabicyclo[2,2,2]-4-octylmethyl phosphate;
(54) 2-acetyloxy-3-hexadecyloxypropyl 7,7-dimethyl-7-azoniabicyclo[2,2,1]-2-heptylmethyl phosphate;
(55) 2-acetyloxy-3-hexadecyloxypropyl 2,2-dimethyl-2-azoniabicyclo[2,2,1]-3-heptylmethyl phosphate;
(56) 2-acetyloxy-3-hexadecyloxypropyl 1-methyl-1-azoniabicyclo[2,2,1]-3-heptylmethyl phosphate;
(57) 2-acetyloxy-3-hexadecyloxypropyl 2,2-dimethyl-1,2,3,4-tetrahydroisoquinolinio-3-ylmethyl phosphate;
(58) 2-acetyloxy-3-octadecyloxypropyl 2,2-dimethyl-1,2,3,4-tetrahydroisoquinolinio-3-ylmethyl phosphate;
(59) 3-acetyloxy-2-hexadecyloxypropionyloxypropyl 2,2-dimethyl-1,2,3,4-tetrahydroquinolinio-3-ylmethyl phosphate;
(60) 2-acetyloxy-3-hexadecyloxypropyl 1,1-dimethyl-1,2,3,4-tetrahydroquinolinio-2-ylmethyl phosphate;
(61) 2-acetyloxy-3-hexadecyloxypropyl 1,1-diethyl-1,2,3,4-tetrahydroquinolinio-2-ylmethyl phosphate;
(62) 2-acetyloxy-3-hexadecyloxybutyl 1,1-dimethyl-1,2,3,4-tetrahydroquinolinio-2-ylmethyl phosphate;

(63) 2-acetyloxy-3-hexadecyloxypropyl 3,3-dimethyl-1,3-thiazolidinio-4-ylmethyl phosphate;
(64) 2-acetyloxy-3-hexadecyloxypropyl 3,3,5,5-tetramethyl-1,3-thiazolidinio-4-ylmethyl phosphate;
(65) 2-acetyloxy-3-hexadecyloxybutyl 3,3-dimethyl-1,3-thiazolidinio-4-ylmethyl phosphate;
(66) 2-acetyloxy-3-hexadecyloxypropyl 3,3-dimethyl-2-phenyl-1,3-thiazolidinio-4-ylmethyl phosphate;
(67) 2-acetyloxy-3-hexadecyloxypropyl 3,3-dimethyl-2-(2-pyridyl)-1,3-thiazolidinio-4-ylmethyl phosphate;
(68) 2-acetyloxy-3-hexadecyloxypropyl 3,3,5,5-tetraimethyl-2-phenyl-1,3-thiazolidinio-4-ylmethyl phosphate;
(69) 2-acetyloxy-3-hexadecyloxybutyl 3,3-dimethyl-2-phenyl-1,3-thiazolidinio-4-ylmethyl phosphate;
(70) 2-acetyloxy-3-hexadecyloxypropyl 3,3-dimethyl-2-(2-methyl)propyl-1,3-thiazolidinio-4-ylmethyl phosphate;
(71) 2-acetyloxy-3-hexadecyloxypropyl 1,1-dimethyl-1,2,5,6-tetrahydropyridinio-3-ylmethyl phosphate;
(72) 2-acetyloxy-3-hexadecyloxybutyl 1,1-dimethyl-1,2,5,6-tetrahydropyridinio-3-ylmethyl phosphate;
(73) 2-acetyloxy-3-hexadecyloxypropyl 3,4-dimethylthiazolio-5-ylethyl phosphate;
(74) 2-acetyloxy-3-hexadecyloxypropyl 3-methyl-4-methylthiazolio-5-ylethyl phosphate;
(75) 2-acetyloxy-3-hexadecyloxypropyl 3-benzyl-4-methylthiazolio-5-ylethyl phosphate;
(76) 2-acetyloxy-3-hexadecyloxypropyl 1-(3,4-dimethylthiazolio-5-yl)ethyl phosphate;
(77) 2-acetyloxy-3-hexadecyloxypropyl 3,4-dimethylthiazolio-5-ylmethyl phosphate;
(78) 2-acetyloxy-3-octadecyloxypropyl 3,4-dimethylthiazolio-5-ylethyl phosphate;
(79) 3-hexadecyloxy-2-propionyloxypropyl 3,4-dimethylthiazolio-5-ylethyl phosphate;
(80) 2-acetyloxy-3-hexadecyloxybutyl 3,4-dimethylthiazolio-5-ylethyl phosphate;
(81) 2-acetyloxy-3-hexadecyloxybutyl 3-benzyl-4-methylthiazolio-5-ylethyl phosphate;
(82) 2-acetyloxy-3-hexadecyloxybutyl 1-(3,4-dimethylthiazolio-5-yl)ethyl phosphate;
(83) 2-acetyloxy-3-hexadecyloxybutyl 1-(2,3,4-trimethylthiazolio-5-yl)ethyl phosphate;
(84) 2-acetyloxy-3-hexadecyloxypropyl 1-methylpyridinio-3-ylethyl phosphate;
(85) 2-acetyloxy-3-hexadecyloxypropyl 1-methylpyridinio-3-ylmethyl phosphate;
(86) 2-acetyloxy-3-hexadecyloxypropyl 3-(1-methylpyridinio-3-yl)-2-propeyl phosphate;
(87) 2-acetyloxy-3-octadecyloxypropyl 1-methylpyridinio-3-ylethyl phosphate;
(88) 2-acetyloxy-3-hexadecyloxybutyl 1-methylpyridinio-3-ylethyl phosphate;
(89) 2-acetyloxy-3-hexadecyloxypropyl 1,1-dimethyl-4-phenylpiperidinio-3-ylmethyl phosphate;
(90) 2-acetyloxy-3-hexadecyloxybutyl 1,1-dimethyl-4-phenylpiperidinio-3-ylmethyl phosphate;
(91) 2-acetyloxy-3-hexadecyloxypropyl 2-methylisoquinolinio-3-ylmethyl phosphate;
(92) 2-acetyloxy-3-hexadecyloxypropyl 1-phenyl-2-methylisoquinolinio-3-ylmethyl phosphate;
(93) 2-acetyloxy-3-hexadecyloxypropyl 1-(1-fluorophenyl)-2-methylisoquinolinio-3-ylmethyl phosphate;
(94) 2-acetyloxy-3-hexadecyloxybutyl 1-(1-chlorophenyl)-2-methylisoquinolinio-3-ylmethyl phosphate;
(95) 2-acetyloxy-3-hexadecyloxypropyl 1,1-dimethylpyrrolio-2-ylmethyl phosphate;
(96) 2-acetyloxy-3-hexadecyloxypropyl 3,4-dimethyloxazolio-5-ylethyl phosphate;
(97) 2-acetyloxy-3-hexadecyloxypropyl 3,4-dimethyloxazolio-5-ylmethyl phosphate;
(98) 2-acetyloxy-3-hexadecyloxypropyl 2,2-dimethyl-2-azoniabicyclo[2,2,1]-6-heptyl phosphate;
(99) 2-acetyloxy-3-hexadecyloxypropyl 2-ethyl-2-methyl-2-azoniabicyclo[2,2,1]-6-heptyl phosphate;
(100) 2-acetyloxy-3-hexadecyloxypropyl 2,2-dimethyl-2-azoniabicyclo[2,2,1]-5-heptyl phosphate;
(101) 2-acetyloxy-3-hexadecyloxypropyl 7,7-dimethyl-7-azoniabicyclo[2,2,1]-2-heptyl phosphate;
(102) 2-acetyloxy-3-hexadecyloxypropyl 8,8-dimethyl-8-azoniabicyclo[3,2,1]-3-octyl phosphate;
(103) 2-acetyloxy-3-hexadecyloxypropyl 8,8-dimethyl-8-azoniabicyclo[3,2,1]-2-octyl phosphate;
(104) 2-acetyloxy-3-hexadecyloxypropyl 3,3-dimethyl-3-azoniabicyclo[3,3,1]-7-nonyl phosphate;
(105) 2-acetyloxy-3-hexadecyloxypropyl 1-methyl-1-azoniabicyclo[2,2,1]-3-heptyl phosphate;
(106) 2-acetyloxy-3-hexadecyloxypropyl 1-methyl-1-azoniabicyclo[2,2,2]-3-octyl phosphate;
(107) 2-acetyloxy-3-hexadecyloxypropyl 1-methyl-1-azoniabicyclo[3,2,1]-3-octyl phosphate;
(108) 2-acetyloxy-3-hexadecyloxypropyl 1-methyl-1-azoniabicyclo[3,3,1]-3-nonyl phosphate;
(109) 2-acetyloxy-3-hexadecyloxypropyl 1-methyl-1-azoniabicyclo[2,2,2]-4-octyl phosphate;
(110) 2-acetyloxy-3-heptadecyloxypropyl 8,8-dimethyl-8-azoniabicyclo[3,2,1]-3-octyl phosphate;
(111) 2-acetyloxy-3-octadecyloxypropyl 1-methyl-1-azoniabicyclo[2,2,2]-3-octyl phosphate;
(112) 2-acetyloxy-3-nonadecyloxypropyl 8,8-dimethyl-8-azoniabicyclo[3,2,1]-3-octyl phosphate;
(113) 3-hexadecyloxy-2-propionyloxypropyl 8,8-dimethyl-8-azoniabicyclo[3,2,1]-3-octyl phosphate;
(114) 2-benzoyloxy-3-hexadecyloxypropyl 8,8-dimethyl-8-azoniabicyclo[3,2,1]-3-octyl phosphate;
(115) 3-hexadecyloxy-2-propionyloxypropyl 1-methyl-1-azoniabicyclo[2,2,2]-3-octyl phosphate;
(116) 2-acetyloxy-3-hexadecyloxybutyl 8,8-dimethyl-8-azoniabicyclo[3,2,1]-3-octyl phosphate;
(117) 2-acetyloxy-3-octadecyloxybutyl 8,8-dimethyl-8-azoniabicyclo[3,2,1]-3-octyl phosphate;
(118) 2-acetyloxy-3-hexadecyloxy-1-methylpropyl 8,8-dimethyl-8-azoniabicyclo[3,2,1]-3-octyl phosphate;
(119) 2-acetyloxy-3-hexadecyloxy-2-methylpropyl 8,8-dimethyl-8-azoniabicyclo[3,2,1]-3-octyl phosphate;
(120) 2-acetyloxy-3-hexadecyloxy-1-methylbutyl 8,8-dimethyl-8-azoniabicyclo[3,2,1]-3-octyl phosphate;
(121) 2-acetyloxy-3-hexadecyloxy-1-(1-methylethyl)propyl 8,8-dimethyl-8-azoniabicyclo[3,2,1]-3-octyl phosphate;
(122) 2-acetyloxy-3-hexadecyloxybutyl 1-methyl-1-azoniabicyclo[2,2,2]-3-octyl phosphate;
(123) 2-acetyloxy-3-octadecyloxybutyl 1-methyl-1-azoniabicyclo[2,2,2]-3-octyl phosphate;
(124) 2-acetyloxy-3-hexadecyloxypropyl 1-methyl-1-azoniabicyclo[2,2,2]-3-octyl phosphate;
(125) 2-acetyloxy-3-hexadecyloxy-2-methylpropyl 1-methyl-1-azoniabicyclo[2,2,2]-6-heptyl phosphate;
(126) 2-acetyloxy-3-hexadecyloxy-1-methylbutyl 1-methyl-1-azoniabicyclo[2,2,2]-3-octyl phosphate;
(127) 2-acetyloxy-3-hexadecyloxy-1-(1-methylethyl)propyl 1-methyl-1-azoniabicyclo[2,2,2]-3-octyl phosphate;
(128) 2-benzyloxy-3-hexadecyloxypropyl 1,1-dimethylpiperidinio-3-yl phosphate;

(129) 2-benzyloxy-3-octadecyloxypropyl 1,1-dimethylpiperidinio-3-yl phosphate;
(130) 2-benzhydryloxy-3-hexadecyloxypropyl 1,1-dimethylpiperidinio-3-yl phosphate;
(131) 2-phenylethyloxy-3-hexadecyloxypropyl 1,1-dimethylpiperidinio-3-yl phosphate;
(132) 2-benzyloxy-3-hexadecyloxybutyl 1,1-dimethylpiperidinio-3-yl phosphate;
(133) 2-benzyloxy-3-hexadecyloxypropyl 1,1-dimethylpiperidinio-4-yl phosphate;
(134) 2-benzyloxy-3-hexadecyloxypropyl 1,1-dimethylpiperidinio-2-ylmethyl phosphate;
(135) 2-benzyloxy-3-octadecyloxypropyl 1,1-dimethylpiperidinio-2-ylmethyl phosphate;
(136) 2-benzhydryloxy-3-hexadecyloxypropyl 1,1-dimethylpiperidinio-2-ylmethyl phosphate;
(137) 2-phenylethyloxy-3-hexadecyloxypropyl 1,1-dimethylpiperidinio-2-ylmethyl phosphate;
(138) 2-benzyloxy-3-hexadecyloxybutyl 1,1-dimethylpiperidinio-2-ylmethyl phosphate;
(139) 2-trityloxy-3-hexadecyloxypropyl 1,1-dimethylpiperidinio-2-ylmethyl phosphate;
(140) 2-benzyloxy-3-hexadecyloxypropyl 1,1-dimethylpiperidinio-2-ylphenylmethyl phosphate;
(141) 2-benzyloxy-3-hexadecyloxypropyl 1,1-dimethylpyrrolidinio-2-ylmethyl phosphate;
(142) 2-benzyloxy-3-octadecyloxypropyl 1,1-dimethylpyrrolidinio-2-ylmethyl phosphate;
(143) 2-benzyloxy-3-hexadecyloxypropyl 1,1-dimethylpyrrolidinio-2-ylethyl phosphate;
(144) 2-benzyloxy-3-hexadecyloxybutyl 1,1-dimethylpyrrolidinio-2-ylethyl phosphate;
(145) 2-benzyloxy-3-hexadecyloxypropyl 1,1-dimethylpyrrolidinio-2-ylphenylmethyl phosphate;
(146) 2-benzyloxy-3-hexadecyloxypropyl 2-(1,1-dimethylpiperidinio-2-yl)-1-phenylethyl phosphate;
(147) 2-benzyloxy-3-hexadecyloxypropyl 2-(1,1-dimethylpiperidinio-2-yl)-2-phenylethyl phosphate;
(148) 2-benzyloxy-3-hexadecyloxypropyl 1,1-dimethylpiperidinio-4-ylmethyl phosphate;
(149) 2-benzyloxy-3-hexadecyloxypropyl 1,1-dimethylperhydroazepinio-2-ylmethyl phosphate;
(150) 2-benzyloxy-3-hexadecyloxypropyl 1-methyl-1-azoniabicyclo[2,2,2]-3-octyl phosphate;
(151) 2-benzyloxy-3-hexadecyloxypropyl 1-methyl-1-azoniabicylo[2,2,2]-3-octylmethyl phosphate;
(152) 2-benzyloxy-3-hexadecyloxypropyl 1-methyl-1-azoniabicyclo[2,2,2]-3-octylphenylmethyl phosphate;
(153) 2-benzyloxy-3-hexadecyloxypropyl 1-methyl-1-azoniabicyclo[2,2,2]-2-octylmethyl phosphate;
(154) 2-benzyloxy-3-hexadecyloxypropyl 8,8-dimethyl-8-azoniabicyclo[3,2,1]-3-octyl phosphate;
(155) 2-benzyloxy-3-hexadecyloxypropyl 8,8-dimethyl-8-azoniabicyclo[3,2,1]-3-octylmethyl phosphate;
(156) 2-benzyloxy-3-hexadecyloxypropyl 8,8-dimethyl-8-azoniabicyclo[3,2,1]-3-octylphenylmethyl phosphate;
(157) 2-benzyloxy-3-hexadecyloxypropyl 8,8-dimethyl-8-azoniabicyclo[3,2,1]-2-octylmethyl phosphate;
(158) 2-cyclohexylmethyloxy-3-hexadecyloxypropyl 1,1-dimethylpyrrolidinio-2-ylmethyl phosphate;
(159) 2-cyclohexyloxy-3-hexadecyloxypropyl 1,1-dimethylpyrrolidinio-2-ylmethyl phosphate;
(160) 2-cyclohexylmethyloxy-3-hexadecyloxypropyl 1,1-dimethylpiperidinio-2-ylmethyl phosphate;
(161) 2-phenoxy-3-hexadecyloxypropyl 1,1-dimethylpyrrolidinio-2-ylmethyl phosphate;
(162) 2-benzyloxy-3-hexadecyloxypropyl 1-methyl-1-azoniabicyclo[3,3,0]-3-octylmethyl phosphate;
(163) 2-acetyloxy-3-hexadecyloxypropyl 1,1-dimethylpyrrolidinio-2-ylphenylmethyl phosphate;
(164) 2-acetyloxy-3-hexadecyloxypropyl 1,1-dimethylpyrrolidinio-2-ylphenylmethyl phosphate;
(165) 2-acetyloxy-3-octadecyloxypropyl 1,1-dimethylpyrrolidinio-2-ylphenylmethyl phosphate;
(166) 2-propionyloxy-3-hexadecyloxypropyl 1,1-dimethylpyrrolidinio-2-ylphenylmethyl phosphate;
(167) 2-acetyloxy-3-hexadecyloxybutyl 1,1-dimethylpyrrolidinio-2-ylphenylmethyl phosphate;
(168) 2-acetyloxy-3-hexadecyloxypropyl 1,1-diethylpyrrolidinio-2-ylphenylmethyl phosphate;
(169) 2-acetyloxy-3-hexadecyloxypropyl 2-(1,1-dimethylpyrrolidinio-2-yl)-1-phenylmethyl phosphate;
(170) 2-acetyloxy-3-hexadecyloxypropyl 2-(1,1-dimethylpyrrolidinio-2-yl)-2-phenylethyl phosphate;
(171) 2-benzyloxy-3-hexadecyloxypropyl 1,1-dimethylpyrrolidinio-2-ylphenylmethyl phosphate;
(172) 2-acetyloxy-3-hexadecyloxypropyl 1,1-dimethylpiperidinio-2-ylphenylmethyl phosphate;
(173) 2-acetyloxy-3-hexadecyloxypropyl 1,1-dimethylpiperidinio-3-ylphenylmethyl phosphate;
(174) 2-acetyloxy-3-hexadecyloxybutyl 1,1-dimethylpiperidinio-2-ylphenylmethyl phosphate;
(175) 2-acetyloxy-3-octadecyloxypropyl 1,1-dimethylpiperidinio-2-ylphenylmethyl phosphate;
(176) 2-acetyloxy-3-hexadecyloxypropyl 2-(1,1-dimethylpiperidinio-2-yl)-2-phenylmethyl phosphate;
(177) 2-acetyloxy-1-hexadecyloxypropyl 2-(1,1-dimethylpiperidinio-2-yl)-2-phenylethyl phosphate;
(178) 2-acetyloxy-3-hexadecyloxypropyl 1-methyl-1-azoniabicyclo[2,2,2]-3-octylphenylmethyl phosphate;
(179) 2-acetyloxy-3-octadecyloxypropyl 1-methyl-1-azoniabicyclo[2,2,2]-3-octylphenylmethyl phosphate;
(180) 2-acetyloxy-3-hexadecyloxypropyl 1-methyl-1-azoniabicyclo[2,2,2]-2-octylphenylmethyl phosphate;
(181) 2-acetyloxy-3-hexadecyloxypropyl 1-methyl-1-azoniabicyclo[2,2,2]-4-octylphenylmethyl phosphate;
(182) 2-acetyloxy-3-hexadecyloxypropyl 1-methyl-1-azoniabicyclo[3,3,0]-3-octylphenylmethyl phosphate;
(183) 2-acetyloxy-3-hexadecyloxypropyl 1-methyl-1-azoniabicyclo[4,4,0]-5-octylphenylmethyl phosphate; and
(184) 2-acetyloxy-3-hexadecyloxypropyl 1-methyl-1-azoniabicyclo[2,2,1]-3-heptylphenylmethyl phosphate.

The compounds having the formula (I) of the present invention may be in the form of a variety of isomers arising from the presence of an asymmetric carbon.

The compound of the formula (I) can be prepared by prepared by acylating a compound having the formula (II):

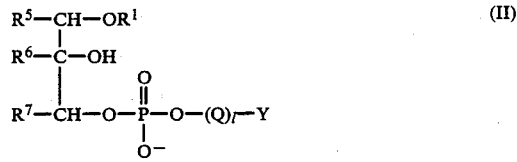

wherein each of $R^1$, $R^5$, $R^6$ and $R^7$ independently has the same meaning as above, and each of Q, l and Y has the same meaning as above, with an acylating agent containing the group $R^2$ that is a straight or branched chain acyl group having 1–6 carbon atoms or benzoyl. Generally, the acylating agent is an acid anhydride($R^2$—O—$R^2$) or an acyl chloride($R^2$—Cl).

The acylating reaction can be carried out in an appropriate organic solvent in the presence of a base. The base may be an ordinary base such as pyridine or triethylamine. If necessary, a catalyst such as 4-dimethylaminopyridine may be employed. Examples of the organic solvents include halogenated hydrocarbons such as methylene chloride, ethylene chloride, chloroform, carbon tetrachloride. In place of using an organic solvent, the acylating agent or a base can be employed as a solvent.

There are no specific limitations with respect to the reaction temperature and the reaction period. Generally, the reaction temperature ranges from 0° C. to a boiling point of a solvent employed, and the reaction period ranges from 30 minutes to 24 hours.

After the acylating reaction is complete, the solvent is distilled off, and if necessary then purified by gel chromatography, to obtain a desired compound as a pure product.

The above-mentioned starting compound of the formula (II) is a novel compound and can be prepared by the following steps:

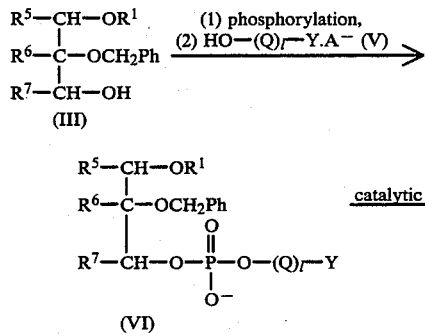

In the above formulae, Ph is phenyl, $A^-$ is an anion such as chlorine ion, bromine ion, iodine ion or tosyl ion, each of $R^1$, $R^5$, $R^6$ and $R^7$ independently has the same meaning as above, and each of Q, l and Y has the same meaning as above.

A starting compound having the formula (III) wherein $R^1$ is hexadecyl, and each of $R^5$, $R^6$ and $R^7$ is hydrogen is already known as described in D. Arnold et al., Liebigs Ann. Chem., vol. 709, pp. 234–239(1967). Other compounds represented by the formula (III) can be prepared in similar manners to those described in the above publication.

The phosphorylation can be carried out using a phosphoryl derivative such as phosphorus oxychloride, and the product is then reacted with a compound of the formula (V). The phosphorylated product can be hydrolyzed and reacted with a compound of the formula (V) in the presence of an activating reagent. After the reaction is complete, the resulting product is treated with an ion exchange resin or a silver salt such as silver carbonate or silver acetate to yield a compound of the formula (VI).

The compound of the formula (VI) is then subjected to catalytic reduction for removing its benzyl group to yield a compound of the formula (II). The catalytic reduction can be carried out under hydrogen atmosphere in the presence of a hydrogenation catalyst such as palladium-carbon, palladium black or platinum dioxide.

The reactions described above are essentially known, and a solvent, a reaction temperature and a reaction period can be chosen according to the known conditions.

Alternatively, the compound of the formula (I) according to the present invention can be prepared by other processes. For instance, the compound of the formula (I) can be prepared by reacting a compound having the formula (X):

wherein each of $R^1$, $R^2$, $R^5$, $R^6$ and $R^7$ independently has the same meaning as above, with phosphorus oxychloride (i.e., phosphoryl chloride) and a compound having the formula (V):

$$H-O-(Q)_l-Y.A^- \quad (V)$$

wherein each of Q, l, Y and $A^-$ has the same meaning as above, in the presence of a base.

The above alternative process can be carried out by the following steps:

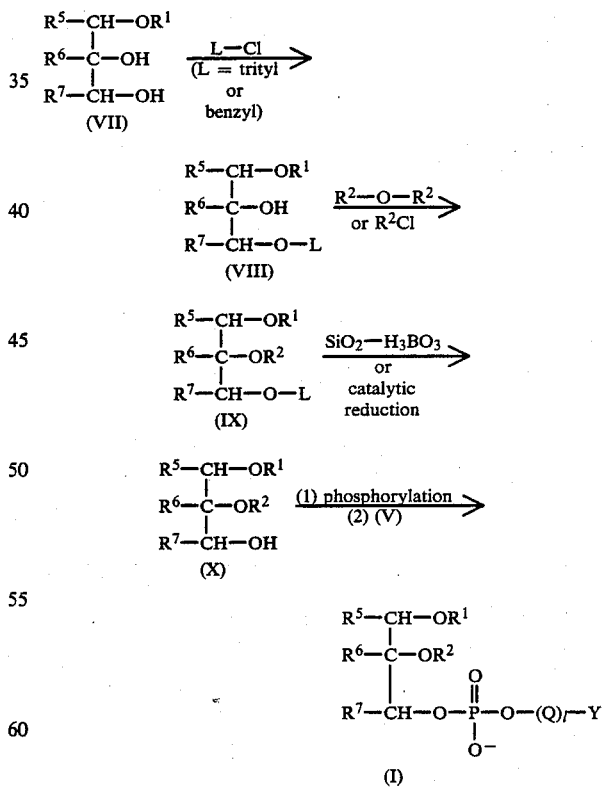

In the above formulae, each of $R^1$, $R^5$, $R^6$ and $R^7$ independently has the same meaning as above, and each of Q, l and Y has the same meaning as above.

The above process comprises a step of acylation in advance of a step of phosphorylation.

A compound in the "sn" form having the formula (X) wherein $R^1$ is hexadecyl, and each of $R^5$, $R^6$ and $R^7$ is hydrogen is already known as described in Synthesis, 1982, pp. 399–402. Other compounds represented by the formula (X) can be prepared in similar manners to those described in the above publication.

The reactions described above are essentially known, and a solvent, a reaction temperature and a reaction period can be chosen according to the known conditions.

Blood pressure reducing actions and blood platelet aggregation action of the glycerol derivatives of the present invention are described by the following pharmacological experimental data.

Blood Pressure Reducing Action: Intravenous Injection

[Procedure]

Male Wistar rats (mean body weight: 420 g) were anesthetized by intraperitoneal injection of 50 mg/kg of pentobarbital sodium, and their blood pressures were measured at left femoral artery. Subsequently, a compound to be tested was dissolved in a saline solution containing 0.25% bovine serum albumin and injected into the rat through the right femoral artery.

[Experimental Results]

A dose-response curve was prepared from the obtained values for each of the following compounds of the present invention to determine a dose required for reducing a mean blood pressure by 50 mmHg ($MABP_{50}$).

$MABP_{50}$ values determined for the compounds of the present invention are given below:

(A) 2-acetyloxy-3-hexadecyloxypropyl 1-methyl-1-azoniabicyclo[2,2,2]-3-octyl phosphate (Example 2 given hereinafter):

$MABP_{50} = 5$ ng/kg (B) 2-acetyloxy-3-hexadecyloxypropyl endo-8,8-dimethyl-8-azoniabicyclo[3,2,1]-3-octyl phosphate (Example 4):

$MABP_{50} = 120$ ng/kg (C) 2-acetyloxy-3-hexadecyloxybutyl 1-methyl-1-azoniabicyclo[2,2,2]-3-octyl phosphate (Example 6):

$MABP_{50} = 99$ ng/kg (D) 2-acetyloxy-3-hexadecyloxypropyl 1,1-dimethyl-pyrrolidinio-2-ylmethyl phosphate (Example 8):

$MABP_{50} = 24$ ng/kg (E) 2-acetyloxy-3-hexadecyloxypropyl 1,1-dimethyl-piperidinio-2-ylmethyl phosphate (Example 10):

$MABP_{50} = 132$ ng/kg (F) 2-acetyloxy-3-hexadecyloxypropyl 1,1-dimethyl-piperidinio-3-ylmethyl phosphate (Example 12):

$MABP_{50} = 58$ ng/kg (G) 2-acetyloxy-3-hexadecyloxypropyl 1,1-dimethyl-piperidinio-4-ylmethyl phosphate (Example 14):

$MABP_{50} = 970$ ng/kg (H) 2-acetyloxy-3-hexadecyloxypropyl 2-(1,1-dimethyl-pyrrolidinio-2-yl)ethyl phosphate (Example 16):

$MABP_{50} = 58$ ng/kg (O) 2-acetyloxy-3-hexadecyloxypropyl 2,2-dimethyl-1,2,3,4-tetrahydroisoquinolinio-3-ylmethyl phosphate (Example 27):

$MABP_{50} = 3.2$ μg/kg (P) 2-acetyloxy-3-hexadecyloxypropyl 1,1-dimethyl-1,2,3,4-tetrahydroquinolinio-2-ylmethyl phosphate (Example 29):

$MABP_{50} = 110$ ng/kg (Q) 2-acetyloxy-3-hexadecyloxypropyl 3,3-dimethyl-1,3-thiazolidinio-4-ylmethyl phosphate (Example 30):

$MABP_{50} = 32$ ng/kg (R) 2-acetyloxy-3-hexadecyloxypropyl 1,1-dimethyl-1,2,5,6-tetrahydropyridinio-3-ylmethyl phosphate (Example 31):

$MABP_{50} = 24$ ng/kg (S) 2-acetyloxy-3-hexadecyloxypropyl 3,3-dimethyl-2-phenyl-1,3-thiazolidinio-4-ylmethyl phosphate (Example 32):

$MABP_{50} = 160$ ng/kg (Product A)

$MABP_{50} = 350$ ng/kg (Product B)

(T) 2-acetyloxy-3-hexadecyloxypropyl 3,4-dimethyl-thiazolio-5-ylethyl phosphate (Example 33):

$MABP_{50} = 0.23$ ng/kg (U) 2-acetyloxy-3-hexadecyloxypropyl 1-methylpyridinio-3-ylethyl phosphate (Example 34):

$MABP_{50} = 195$ ng/kg (V) 2-acetyloxy-3-hexadecyloxybutyl 1,1-dimethyl-1,2,5,6-tetrahydropyridinio-3-ylmethyl phosphate (Example 40):

$MABP_{50} = 640$ ng/kg (W) 2-acetyloxy-3-hexadecyloxybutyl 3,4-dimethyl-thiazolio-5-ylethyl phosphate (Example 42):

$MABP_{50} = 67$ ng/kg

Blood Pressure Reducing Action: Oral Administration

[Procedure]

Male spontaneously hypertensive rats (average body weight: 359 g) were anesthetized with ether. Blood pressure was measured for each rat through cannulation at its left femoral artery. A compound to be tested was dissolved in a distilled water and the resulting aqueous solution was administered orally.

| Compound | [Experimental Results] | | | | |
|---|---|---|---|---|---|
| | None | C | T | V | W |
| Dose(mg/kg) | — | 3 | 10 | 3 | 1 |
| Number of Sample | 2 | 4 | 3 | 2 | 3 |
| Mean Blood Pressure before Administration (mmHg) | 155.0 | 52.5 | 141.0 | 138.0 | 150.3 |
| Change of Blood Pressure (mmHg) About 30 min. after Administration | +5.0 | −64.5 | −35.3 | −49.0 | −36.0 |

Remark: Compounds C, T and V are the same as described above.

Platelet Aggregation Action

[Procedure]

A male Japanese white rabbit was anesthetized by pentobarbital, and a blood was collected in aqueous 3.13% sodium citrate solution at its carotid. The blood containing 1/10 volume ratio of the sodium citrate solution was treated in a conventional manner to give a platelet rich plasma (PRP) and a platelet poor plasma (PPP) for performing the following experiment.

PRP was diluted with PPP to give a sample containing platelets at 300,000/mm$^3$.

Aggregation of platelet was determined by means of Platelet Aggregation Tracer PAT-4A(available from Niko Bioscience Co., Ltd., Japan). 10 μl of a test solution was added to 190 μl of PRP to give a final concentration of $2 \times 10^{-10}$ to $2 \times 10^{-4}$M, and an aggregation curve is recorded. For the preparation of the test solution, a saline solution containing 0.25% bovine serum albumin.

[Results]

According to the aggregation curve obtained for each of the following compound of the present invention, following $EC_{50}$ value was obtained.

| Compound | $EC_{50}$ |
| --- | --- |
| A | $7.6 \times 10^{-10}$ |
| B | $2.3 \times 10^{-9}$ |
| C | $5.2 \times 10^{-9}$ |
| D | $5.0 \times 10^{-10}$ |
| E | $1.0 \times 10^{-8}$ |
| F | $1.5 \times 10^{-9}$ |
| G | $9.0 \times 10^{-8}$ |
| H | $2.4 \times 10^{-9}$ |
| O | $1.8 \times 10^{-7}$ |
| P | $5.0 \times 10^{-8}$ |
| Q | $5.2 \times 10^{-10}$ |
| S(Product A) | $6.7 \times 10^{-7}$ |
| S(Product B) | $7.4 \times 10^{-7}$ |
| T | $3.2 \times 10^{-9}$ |
| U | $8.5 \times 10^{-8}$ |
| V | $7.7 \times 10^{-8}$ |
| W | $7.3 \times 10^{-8}$ |

As is clear from the above experimental data, the glycerol derivatives of the present invention show prominent blood pressure reducing action, while show troublesome blood platelet agglutination action at a lower level.

Inhibitory Effect on PAF-induced Platelet Aggregation

[Procedure]

In the same manner as above, a platelet rich plasma (PRP) and a platelet poor plasma (PPP) were prepared for performing the following experiment.

PRP was diluted with PPP to give a sample containing platelets at $300,000/mm^3$.

10 μl of a test solution was added to 180 μl of PRP. To the resulting mixture was added 10 μl of a solution of a commercially available PAF (No.P-4904, available from Sigma Corp.) to give a concentration of $1 \times 10^{-8}M$, and aggregation was observed. For the preparation of the test solution and the PAF solution, a saline solution containing 0.25% bovine serum albumin was employed.

The effect of the test sample for suppressing aggregation was obtained in terms of a degree of suppression of the maximum aggregation in the control PRP caused by the PAF.

| Tested Compound | [Results] Concentration of Test Solution $2 \times 10^{-4}$ M |
| --- | --- |
| I | 100% |
| J | 99% |
| K | 73% |
| L | 55% |
| M | 100% |
| N | 100% |

-continued

| Tested Compound | [Results] Concentration of Test Solution $2 \times 10^{-4}$ M |
| --- | --- |
| X | 100% |

Remarks:
I 2-benzyloxy-3-hexadecyloxybutyl erythro-1,1-dimethylpyrrolidinio-2-ylphenylmethyl phosphate (Example 22)
J 2-benzyloxy-3-hexadecyloxypropyl erythro-1,1-dimethylpyrrolidinio-2-ylphenylmethyl phosphate (Example 23)
K 2-benzyloxy-3-hexadecyloxypropyl threo-1,1-dimethylpyrrolidinio-2-ylphenylmethyl phosphate (Example 24)
L 2-benzyloxy-3-hexadecyloxypropyl 1,1-dimethyl-piperidinio-2-ylmethyl phosphate (Example 9)
M 2-acetyloxy-3-hexadecyloxypropyl erythro-1,1-dimethylpyrrolidinio-2-ylphenylmethyl phosphate (Example 25)
N 2-acetyloxy-3-hexadecyloxypropyl threo-1,1-dimethylpyrrolidinio-2-ylphenylmethyl phosphate (Example 26)
X 2-acetyloxy-3-hexadecyloxypropyl 1-(1-fluoro-phenyl)-2-methylisoquinolinio-3-ylmethyl phosphate (Example 39)

As is apparent, the glycerol derivatives of the invention is effective in inhibiting aggregation of platelet in the presence of PAF.

Further, it has been confirmed that the new glycerol derivative of the invention shows an anti-tumor action.

The glycerol derivative of the present invention can be incorporated into a pharmaceutical composition in the form of tablets, granules, powder, capsule, syrup, suppository, injection liquid etc. The glycerol derivative is generally adiminstered to human being at a dose of 10 μg/kg to 0.5 mg/kg. The pharmaceutical composition of such dose can be administered 1–4 times a day depending on conditions of patients. Thus, the dose can vary depending upon conditions of patient, procedure of administration, etc. The pharmaceutical compositions can contain a carrier, a vehicle, a diluent, etc.

The processes for the preparation of the glycerol derivatives of the present invention and the pharmaceutical compositions are further described by the following examples. The phosphates expressed in the following examples are in the form of inner salts. The reference examples are given to describe starting compounds and intermediate compound employed for the preparation of the glycerol derivatives of the present invention.

REFERENCE EXAMPLE 1

1-Methyl-3-hydroxy-1-azoniabicyclo[2,2,2]octane p-toluenesulfonate

In 10 ml of acetone was dissolved 1.27 g of quinuclidinol, and 1.86 g of methyl p-toluenesulfonate was added dropwise to the resulting solution. The mixture was stirred at room temperature, heated under reflux, and cooled to precipitate crystals. The crystals were collected by filtration and dried to give 2.81 g of the desired product.

$^1$H NMR (CD$_3$OD)δ: 1.5–3.8 (m, 11H), 2.34 (s, 3H), 2.94 (s, 3H), 4.0–4.2 (m, 1H), 7.1–7.7 (m, 4H).

IR (KBr) cm$^{-1}$: 3350, 2950, 1460, 1320, 1220, 1180, 1120, 1030, 1005, 820, 680, 560.

EXAMPLE 1

2-Benzyloxy-3-hexadecyloxypropyl 1-methyl-1-azoniabicyclo[2,2,2]-3-octyl phosphate In 3 ml of ethanol-free chloroform was dissolved 0.1 ml of phosphorus oxychloride and 0.3 ml of triethylamine under nitrogen atmosphere, and the obtained solution was stirred for a while at room temperature. To the solution was dropwise added under chilling 3 ml of a solution of 406 mg of 2-benzyloxy-3-hexadecyloxy-1- propanol in chloroform. After the addition was complete, the mixture was stirred for 1 hour at room temperature, and to the mixture were added a solution of 500 mg of 1-methyl-3-hydroxy-1-azoniabicyclo[2,2,2]octane p-toluenesulfonate (prepared in Reference Example 1) in 8 ml of dry pyridine. The mixture was stirred overnight at room temperature and to the mixture were added 500 mg of sodium hydrogencarbonate and 1 ml of water. The solvent was then distilled off under reduced pressure. To the residue was added 15 ml of a mixture of toluene and methylene chloride (v/v=1/1), and insolubles were filtered off. The filtrate was concentrated under reduced pressure, and the resulting residue was dissolved in a mixture of tetrahydrofuran and water (v/v=95/5). The solution was passed through a column of ion-exchange resin (Amberlite MB-3), which was then eluted with the same mixture of tetrahydrofuran and water. The eluate was placed under reduced pressure to distill off the solvent. The residue was purified by column chromatography using silica gel (eluent: chloroform/methanol/water=70/30/5) to obtain 190 mg of the desired compound.

$^1$H NMR (CD$_3$OD) δ: 0.90 (t, 3H), 1.28 (s, 26H), 1.3–4.6 (m, 24H), 4.66 (s, 2H), 7.1–7.4 (m, 5H).

IR (KBr) cm$^{-1}$: 3380, 2900, 2830, 1460, 1220, 1110, 1080, 1070, 1040, 1015, 995, 950, 900, 840, 815, 740, 690, 590, 515.

EXAMPLE 2

2-Acetyloxy-3-hexadecyloxypropyl 1-methyl-1-azoniabicyclo[2,2,2]-3-octyl phosphate (1) In 20 ml of ethanol was dissolved 170 mg of 2-benzyloxy-3-hexadecyloxypropyl 1-methylazoniabicyclo[2,2,2]-3-octyl phosphate prepared in Example 1, and 30 mg of palladium(5%)-carbon (catalyst) was added to the resulting solution. The mixture was stirred overnight at room temperature in a stream of hydrogen. The catalyst was removed from the reaction liquid by filtration. The filtrate was concentrated under reduced pressure to give 140 mg of 3-hexadecyloxy-2-hydroxypropyl 1-methyl-1-azoniabicyclo[2,2,2]-3-octyl phosphate.

$^1$H NMR (CD$_3$OD) δ: 0.90 (t, 3H), 1.28 (s, 26H), 1.3–4.7 (m, 24H).

IR (KBr) cm$^{-1}$: 3400, 2900, 2830, 1460, 1220, 1110, 950, 900, 820, 710, 510.

(2) In 13 ml of chloroform were dissolved 130 mg of 3-hexadecyloxy-2-hydroxypropyl 1-methyl-1-azoniabicyclo[2,2,2]-3-octyl phosphate obtained as above and 650 mg of acetic anhydride. To the solution was added 260 mg of triethylamine, and the mixture was heated under reflux overnight. The solvent was then distilled off under reduced pressure, and the resulting residue was purified by silica gel column chromatography (chloroform:methanol:water=70:30:5) to obtain 80 mg of the desired compound.

$^1$H NMR (CD$_3$OD) δ: 0.89 (t, 3H), 1.28 (s, 26H), 1.3–2.5 (m, 7H), 2.04 (s, 3H), 2.8–4.8 (m, 16H), 4.9–5.2 (m, 1H).

IR (KBr) cm$^{-1}$: 3425, 2910, 2850, 1730, 1460, 1370, 1240, 1120, 1070, 1015, 995, 900, 820, 600, 520.

REFERENCE EXAMPLE 2 endo-8,8-Dimethyl-3-hydroxy-8-azoniabicyclo[3,2,1]-octane p-toluenesulfonate

The procedures of Reference Example 1 were repeated using 2.82 g of 3-tropanol and 3.72 g of methyl p-toluenesulfonate to give 5.71 g of the desired compound.

$^1$H NMR (DMSO-d$_6$) δ: 1.5–2.5 (m, 11H), 2.29 (s, 3H), 2.99 (s, 3H), 3.03 (s, 3H), 3.4–4.0 (m, 3H), 4.96 (d, 1H), 6.9–7.5 (m, 4H).

IR (KBr) cm$^{-1}$: 3380, 3035, 3000, 2950, 2920, 1465, 1450, 1325, 1310, 1245, 1220, 1190, 1170, 1130, 1085, 1060, 1040, 1015, 950, 940, 815.

EXAMPLE 3

2-Benzyloxy-3-hexadecyloxypropyl endo-8,8-dimethyl-8-azoniabicyclo[3,2,1]-3-octyl phosphate The procedures of Example 1 were repeated using 407 mg of 2-benzyloxy-3-hexadecyloxy-1-propanol, 491 mg of endo-8,8-dimethyl-3-hydroxy-8-azoniabicyclo[3,2,1]-octane p-toluenesulfonate prepared in Reference Example 2, 0.12 ml of phosphorus oxychloride, 0.35 ml of triethylamine, 6 ml of chloroform, and 10 ml of dry pyridine, to give 132 mg of the desired compound.

$^1$H NMR (CD$_3$OD) δ: 0.89 (t, 3H), 1.28 (s, 26H), 1.3–4.6 (m, 26H), 4.69 (s, 2H), 7.0–7.4 (m, 5H).

IR (KBr) cm$^{-1}$: 3400, 2920, 2845, 1460, 1445, 1215, 1090, 1070, 1055, 1040, 1000, 970.

EXAMPLE 4

2-Acetyloxy-3-hexadecyloxypropyl endo-8,8-dimethyl-8-azoniabicyclo[3,2,1]-3-octyl phosphate (1) The procedures of Example 2-(1) were repeated using 105 mg of 2-benzyloxy-3-hexadecyloxypropyl endo-8,8-dimethyl-8-azoniabicyclo[3,2,1]-3-octyl phosphate prepared in Example 3, 15 mg of palladium(10%)-carbon and 10 ml of ethanol, to give 89 mg of 3-hexadecyloxy-2-hydroxypropyl endo-8,8-dimethyl-8-azoniabicyclo[3,2,1]-3-octyl phosphate.

$^1$H NMR (CD$_3$OD) δ: 0.90 (t, 3H), 1.28 (s, 26H), 1.3–4.6 (m, 26H).

IR (KBr) cm$^{-1}$: 3400, 2910, 2840, 1460, 1450, 1220, 1090, 1075, 1055, 1040, 1005, 970.

(2) The procedures of Example 2-(2) were repeated using 78 mg of 3-hexadecyloxy-2-hydroxypropyl endo-8,8-dimethyl-8-azoniabicyclo[3,2,1]-3-octyl phosphate obtained as above, 373 mg of acetic anhydride, 148 mg of triethylamine and 7 ml of chloroform to give 55 mg of the desired compound.

$^1$H NMR (CD$_3$OD) δ: 0.90 (t, 3H), 1.28 (s, 26H), 1.3–1.7 (m, 2H), 2.05 (s, 3H), 2.1–2.8 (m, 8H), 3.0–4.6 (m, 15H), 4.9–5.2 (m, 1H).

IR (KBr) cm$^{-1}$: 3420, 2925, 2850, 1735, 1465, 1455, 1380, 1240, 1095, 1080, 1040, 1005, 975.

EXAMPLE 5

2-Benzyloxy-3-hexadecyloxybutyl 1-methyl-1-azoniabicyclo[2,2,2]-3-octyl phosphate The procedures of Example 1 were repeated using 1,178 mg of 2-benzyloxy-3-hexadecyloxy-1-butanol, 1,316 mg of 1-methyl-3-hydroxy-1-azoniabicyclo[2,2,2]octane p-toluenesulfonate prepared in Reference Example 1, 0.34 ml of phosphorus oxychloride, 0.98 ml of triethylamine, 15.8 ml of chloroform, and 28 ml of dry pyridine, to give 1,216 mg of the desired compound.

$^1$H NMR (CD$_3$OD) δ: 0.90 (t, 3H), 1.17 (d, 3H), 1.28 (s, 26H), 1.3–4.7 (m, 23H), 4.72 (s, 2H), 7.1–7.55 (m, 5H).

IR (KBr) cm$^{-1}$: 3400, 2920, 2850, 1465, 1450, 1220, 1120, 1110, 1090, 1070, 1050, 1040, 1020, 950.

EXAMPLE 6

2-Acetyloxy-3-hexadecyloxybutyl 1-methyl-1-azoniabicyclo[2,2,2]-3-octyl phosphate (1) The procedures of Example 2-(1) were repeated using 1,199 mg of 2-benzyloxy-3-hexadecyloxybutyl 1-methyl-1-azoniabicyclo[2,2,2]-3-octyl phosphate prepared in Example 5, 120 mg of palladium(10%)-carbon and 80 ml of methanol, to give 945 mg of 3-hexadecyloxy-2-hydroxybutyl 1-methyl-1-azoniabicyclo[2,2,2]-3-octyl phosphate.

$^1$H NMR (CD$_3$OD) δ: 0.90 (t, 3H), 1.17 (d, 3H), 1.28 (s, 26H), 1.3–4.7 (m, 23H).

IR (KBr) cm$^{-1}$: 3400, 2910, 2840, 1465, 1245, 1225, 1120, 1105, 1090, 1070, 1050, 1010, 950.

(2) The procedures of Example 2-(2) were repeated using 876 mg of 3-hexadecyloxy-2-hydroxybutyl 1-methyl-1-azoniabicyclo[2,2,2]-3-octyl phosphate obtained as above, 4186 mg of acetic anhydride, 1660 mg of triethylamine and 80 ml of chloroform to give 804 mg of the desired compound.

$^1$H NMR (CD$_3$OD) δ: 0.90 (t, 3H), 1.15 (d, 3H), 1.29 (s, 26H), 1.3–2.6 (m, 7H), 2.07 (s, 3H), 2.9–4.7 (m, 15H), 4.9–5.2 (m, 1H).

IR (KBr) cm$^{-1}$: 3400, 2920, 2850, 1730, 1465, 1375, 1240, 1120, 1105, 1090, 1080, 1050, 1020.

REFERENCE EXAMPLE 3

1,1-Dimethyl-2-hydroxymethylpyrrolidinium p-toluenesulfonate

In 10 ml of acetone was dissolved 1.47 g of 1-methyl-2-pyrrolidinemethanol, and 2.38 g of methyl p-toluenesulfonate was added dropwise to the resulting solution. The mixture was stirred at room temperature, heated under reflux, and cooled to precipitate crystals. The crystals were collected by filtration and dried to give 2.67 g of the desired compound.

$^1$H NMR (DMSO-d$_6$) δ: 1.5–2.2 (m, 4H), 2.28 (s, 3H), 2.94 (s, 3H), 3.17 (s, 3H), 3.3–3.9 (m, 5H), 5.25–5.5 (m, 1H), 6.95–7.6 (m, 4H).

IR (KBr) cm$^{-1}$: 3400, 3050, 2960, 2900, 1475, 1190, 1130, 1040, 1015, 820, 690, 575.

EXAMPLE 7

2-Benzyloxy-3-hexadecyloxypropyl 1,1-dimethylpyrrolidinio-2-ylmethyl phosphate

In 3 ml of chloroform was dissolved 0.12 ml of phosphorus oxychloride and 0.35 ml of triethylamine under nitrogen atmosphere, and the resulting solution was stirred for a while at room temperature. To the solution was dropwise added under chilling 3 ml of a solution of 407 mg of 2-benzyloxy-3-hexadecyloxy-1-propanol in chloroform. After the addition was complete, the mixture was stirred for 30 minutes at room temperature, and to the mixture were added 452 mg of 1,1-dimethyl-2-hydroxymethylpyrrolidinium p-toluenesulfonate prepared in Reference Example 3 and 10 ml of dry pyridine. The mixture was stirred overnight at room temperature, and 560 mg of sodium hydrogencarbonate and 1.25 ml of water. The solvent was then distilled off under reduced pressure. To the residue was added 15 ml of a mixture of toluene and methylene chloride (v/v=1/1), and insolubles were filtered off. The filtrate was concentrated under reduced pressure, and the resulting residue was dissolved in a mixture of tetrahydrofuran and water (v/v=95/5). The solution was passed through a column of ion-exchange resin (Amberlite MB-3), which was then eluated with the same mixture of tetrahydrofuran and water. The eluate was placed under reduced pressure to distill off the solvent. The residue was purified by column chromatography using silica gel (eluent: chloroform/methanol/water=70/30/5) to obtain 212 mg of the desired compound.

$^1$H NMR (CD$_3$OD) δ: 0.90 (t, 3H), 1.28 (s, 26H), 1.3–1.65 (m, 2H), 1.7–4.1 (m, 22H), 4.69 (s, 2H), 7.1–7.5 (m, 5H).

IR (KBr) cm$^{-1}$: 3400, 3050, 3020, 2920, 2850, 1465, 1230, 1190, 1165, 840.

EXAMPLE 8

2-Acetyloxy-3-hexadecyloxypropyl 1,1-dimethylpyrrolidinio-2-ylmethyl phosphate (1) In 20 ml of ethanol was dissolved 162 mg of 2-Benzyloxy-3-hexadecyloxypropyl 1,1-dimethylpyrrolidinio-2-ylmethyl phosphate prepared in Example 7, and 20 mg of palladium(5%)-carbon (catalyst) was added to the resulting solution. The mixture was stirred overnight at 50° C. in a stream of hydrogen. The reaction liquid was cooled, and the catalyst was removed by filtration. The filtrate was concentrated under reduced pressure to give 111 mg of 3-hexadecyloxy-2-hydroxypropyl 1,1-dimethylpyrrolidinio-2-ylmethyl phosphate.

$^1$H NMR (CD$_3$OD) δ: 0.90 (t, 3H), 1.28 (s, 26H), 1.3–4.3 (m, 24H).

IR (KBr) cm$^{-1}$: 3420, 2920, 2850, 1470, 1230, 1100, 1070, 960, 840, 720, 520.

(2) In 10 ml of chloroform were dissolved 100 mg of 3-hexadecyloxy-2-hydroxypropyl 1,1-dimethyl-1-pyrrolidinio-2-ylmethyl phosphate obtained as above and 503 mg of acetic anhydride. To the solution was added 199 mg of triethylamine, and the mixture was heated under reflux overnight. The solvent was then distilled off under reduced pressure, and the resulting residue was purified by silica gel column chromatography (chloroform:methanol:water=70:30:5) to obtain 100 mg of the desired compound.

$^1$H NMR (CD$_3$OD) δ: 0.89 (t, 3H), 1.28 (s, 26H), 1.3–2.4 (m, 6H), 2.06 (s, 3H), 2.9–4.3 (m, 17H), 4.9–5.2 (m, 1H).

IR (KBr) cm$^{-1}$: 3400, 2925, 2855, 1735, 1470, 1240, 1100, 1070.

REFERENCE EXAMPLE 4

1,1-Dimethyl-2-hydroxymethylpiperidinium p-toluenesulfonate

The procedures of Reference Example 3 were repeated using 2.58 g of 1-methyl-2-piperidinemethanol and 3.72 g of methyl p-toluenesulfonate to give 4.95 g of the desired compound.

$^1$H NMR (CDCl$_3$) δ: 1.3–1.9 (m, 6H), 2.32 (s, 3H), 3.04 (s, 3H), 3.1–3.6 (m, 2H), 3.36 (s, 3H), 3.7–4.0 (m, 2H), 5.34 (t, 1H), 7.0–7.8 (m, 4H).

IR (KBr) cm$^{-1}$: 3325, 2925, 1490, 1470, 1445, 1190, 1125, 1040, 1000, 810, 680, 560.

EXAMPLE 9

2-Benzyloxy-3-hexadecyloxypropyl 1,1-dimethylpiperidinio-2-ylmethyl phosphate

The procedures of Example 7 were repeated using 406 mg of 2-benzyloxy-3-hexadecyloxy-1-propanol, 500 mg of 1,1-dimethyl-4-hydroxymethylpiperidinium p-toluenesulfonate prepared in Reference Example 4, 0.1 ml of phosphorus oxychloride, 0.3 ml of triethylamine, 6 ml of chloroform, and 8 ml of dry pyridine to give 300 mg of the desired compound.

$^1$H NMR (CD$_3$OD) δ: 0.90 (t, 3H), 1.28 (s, 26H), 1.3–4.1 (m, 26H), 4.66 (s, 2H), 7.1–7.4 (m, 5H).

IR (KBr) cm$^{-1}$: 3400, 2920, 1460, 1230, 1080, 830, 740, 690, 520.

EXAMPLE 10

2-Acetyloxy-3-hexadecyloxypropyl 1,1-dimethylpiperidinio-2-ylmethyl phosphate (1) The procedures of Example 8-(1) were repeated using 300 mg of 2-benzyloxy-3-hexadecyloxypropyl 1,1-dimethylpiperidinio-2-ylmethyl phosphate prepared in Example 9, 50 mg of palladium(5%)-carbon and 30 ml of ethanol, to give 220 mg of 3-hexadecyloxy-2-hydroxypropyl 1,1-dimethylpiperidinio-2-ylmethyl phosphate.

$^1$H NMR (CD$_3$OD) δ: 0.90 (t, 3H), 1.28 (s, 26H), 1.3–4.2 (m, 26H).

IR (neat) cm$^{-1}$: 3400, 2910, 2850, 1465, 1220, 1080.

(2) The procedures of Example 8-(2) were repeated using 190 mg of 3-hexadecyloxy-2-hydroxypropyl 1,1-dimethylpiperidinio-2-ylmethyl phosphate obtained as above, 4 ml of acetic anhydride, 1 ml of dry pyridine and 10 ml of ethylene chloride to give 80 mg of the desired compound.

$^1$H NMR (CD$_3$OD) δ: 0.89 (t, 3H), 1.28 (s, 26H), 1.3–2.0 (m, 8H), 2.04 (s, 3H), 3.1–4.3 (m, 17H), 4.9–5.1 (m, 1H).

IR (KBr) cm$^{-1}$: 3400, 2920, 2860, 1740, 1460, 1370, 1250, 1190, 1120, 1090, 1045, 1020, 1000, 980, 945, 810, 720, 690.

REFERENCE EXAMPLE 5

1,1-Dimethyl-3-hydroxymethylpiperidinium p-toluenesulfonate

The procedures of Reference Example 3 were repeated using 2.58 g of 1-methyl-3-piperidinemethanol and 3.72 g of methyl p-toluenesolfonate, to give 5.13 g of the desired compound, m.p. 130°–132° C.

$^1$H NMR (DMSO-d$_6$) δ: 0.8–2.1 (m, 5H), 2.29 (s, 3H), 2.6–3.6 (m, 6H), 3.03 (s, 3H), 3.11 (s, 3H), 4.79 (t, 1H), 6.9–7.6 (m, 4H).

IR (KBr) cm$^{-1}$: 3360, 3050, 3020, 2940, 2910, 2860, 1480, 1450, 1215, 1190, 1045, 1010, 820, 700, 560.

EXAMPLE 11

2-Benzyloxy-3-hexadecyloxypropyl 1,1-dimethylpiperidinio-3-ylmethyl phosphate

The procedures of Example 7 were repeated using 407 mg of 2-benzyloxy-3-hexadecyloxy-1-propanol, 473 mg of 1,1-dimethyl-3-hydroxymethylpiperdinium p-toluenesulfonate prepared in Reference Example 5, 0.12 ml of phosphorus oxychloride, 0.35 ml of triethylamine, 6 ml of chloroform having passed through an alumina column, and 10 ml of dry pyridine, to give 250 mg of the desired compound.

$^1$H NMR (CD$_3$OD) δ: 0.89 (t, 3H), 1.28 (d, 26H), 1.3–4.0 (m, 26H), 4.70 (s, 2H), 7.1–7.5 (m, 5H).

IR (KBr) cm$^{-1}$: 3400, 3060, 3020, 2930, 2860, 1640, 1460, 1220, 1090, 1070.

EXAMPLE 12

2-Acetyloxy-3-hexadecyloxypropyl 1,1-dimethylpiperidinio-3-ylmethyl phosphate (1) The procedures of Example 8-(1) were repeated using 195 mg of 2-benzyloxy-3-hexadecyloxypropyl 1,1-dimethylpiperidinio-3-ylmethyl phosphate prepared in Example 11, 15 mg of palladium(5%)-carbon and 20 ml of ethanol, to give 126 mg of 3-hexadecyloxy-2-hydroxypropyl 1,1-dimethylpiperidinio-3-ylmethyl phosphate.

$^1$H NMR (CD$_3$OD) δ: 0.90 (t, 3H), 1.28 (s, 26H), 1.3–4.0 (m, 26H).

IR (KBr) cm$^{-1}$: 3450, 2930, 2860, 1470, 1230, 1090, 1070, 1040.

(2) The procedures of Example 8-(2) were repeated using 109 mg of 3-hexadecyloxy-2-hydroxypropyl 1,1-dimethylpiperidinio-3-ylmethyl phosphate obtained as above, 534 mg of acetic anhydride, 211 mg of triethylamine, and 10 ml of chloroform to give 75 mg of the desired compound.

$^1$H NMR (CD$_3$OD) δ: 0.89 (t, 3H), 1.28 (s, 26H), 1.3–2.0 (m, 6H), 2.05 (s, 3H), 2.2–4.0 (m, 19H), 4.9–5.2 (m, 1H).

IR (KBr) cm$^{-1}$: 3450, 2925, 2850, 1735, 1470, 1375, 1240, 1095, 1070, 1040.

REFERENCE EXAMPLE 6

1,1-Dimethyl-4-hydroxymethylpiperidinium p-toluenesulfonate

The procedures of Reference Example 3 were repeated using 1.57 g of 1-methyl-4-piperidinemethanol and 2.26 g of methyl p-toluenesolfonate, to give 3.13 g of the desired compound.

$^1$H NMR (DMSO-d$_6$) δ: 1.2–2.0 (m, 4H), 2.27 (s, 3H), 2.96 (s, 3H), 3.06 (s, 3H), 3.1–3.5 (m, 7H), 4.60 (t, 1H), 7.0–7.6 (m, 4H).

IR (KBr) cm$^{-1}$: 3325, 3010, 2950, 2850, 2790, 1470, 1410, 1390, 1310, 1280, 1200, 1125, 1075, 1040, 1010, 920, 810, 670, 565.

EXAMPLE 13

2-Benzyloxy-3-hexadecyloxypropyl 1,1-dimethylpiperidinio-4-ylmethyl phosphate

The procedures of Example 7 were repeated using 812 mg of 2-benzyloxy-3-hexadecyloxy-1-propanol, 1 g of 1,1-dimethyl-4-hydroxymethylpiperdinium p-toluenesulfonate prepared in Reference Example 6, 0.2 ml of phosphorus oxychloride, 0.6 ml of triethylamine, 12 ml of chloroform, and 16 ml of dry pyridine, to give 820 mg of the desired compound.

$^1$H NMR (CD$_3$OD) δ: 0.88 (t, 3H), 1.28 (s, 26H), 1.3–1.9 (m, 6H), 3.00 (s, 3H), 3.08 (s, 3H), 3.0–4.0 (m, 14H), 4.68 (s, 2H), 7.1–7.4 (m, 5H).

IR (KBr) cm$^{-1}$: 3400, 2910, 2850, 1460, 1370, 1340, 1220, 1120, 1070, 1020, 980, 920, 850, 700, 540.

EXAMPLE 14

2-Acetyloxy-3-hexadecyloxypropyl 1,1-dimethylpiperidinio-4-ylmethyl phosphate (1) The procedures of Example 8-(1) were repeated using 770 mg of 2-benzyloxy-3-hexadecyloxypropyl 1,1-dimethylpiperidinio-4-ylmethyl phosphate prepared in Example 13, 150 mg of palladium(5%)-carbon and 100 ml of ethanol, to give 650 mg of 3-hexadecyloxy-2- hydroxypropyl 1,1-dimethylpiperidinio-4-ylmethyl phosphate.

$^1$H NMR (CD$_3$OD) δ: 0.88 (t, 3H), 1.28 (s, 26H), 1.3–2.0 (m, 6H), 3.08 (s, 3H), 3.14 (s, 3H), 3.2–3.9 (m, 14H).

IR (KBr) cm$^{-1}$: 3400, 2910, 2850, 1460, 1220, 1120, 1080, 990, 940, 920, 850.

(2) The procedures of Example 8-(2) were repeated using 600 mg of 3-hexadecyloxy-2-hydroxypropyl 1,1-dimethylpiperidinio-4-ylmethyl phosphate obtained as above, 12 ml of acetic anhydride, and 3 ml of dry pyridine to give 260 mg of the desired compound.

$^1$H NMR (CD$_3$OD) δ: 0.88 (t, 3H), 1.28 (s, 26H), 1.3–2.0 (m, 6H), 2.04 (s, 3H), 3.08 (s, 3H), 3.14 (s, 3H), 3.3–4.5 (m, 13H), 5.0–5.2 (m, 1H).

IR (KBr) cm$^{-1}$: 3400, 2910, 2850, 1730, 1460, 1370, 1280, 1070, 980, 920, 840, 800, 540.

REFERENCE EXAMPLE 7

1,1-Dimethyl-2-(2-hydroxyethyl)pyrrolidinium p-toluenesulfonate

The procedures of Reference Example 3 were repeated using 1 g of 1-methyl-2-pyrrolidineethanol and 1.41 g of methyl p-toluenesolfonate, to give 2 g of the desired compound.

$^1$H NMR (CD$_3$OD) δ: 1.5–2.6 (m, 7H), 2.36 (s, 3H), 2.86 (s, 3H), 3.12 (s, 3H), 3.4–3.8 (m, 4H), 7.1–7.7 (m, 4H).

IR (KBr) cm$^{-1}$: 3350, 2925, 1470, 1180, 1120, 1030, 1000, 850, 680, 560.

EXAMPLE 15

2-Benzyloxy-3-hexadecyloxypropyl 2-(1,1-dimethylpyrrolidinio-2-yl)ethyl phosphate The procedures of Example 7 were repeated using 406 mg of 2-benzyloxy-3-hexadecyloxy-1-propanol, 500 mg of 1,1-dimethyl-2-(2-hydroxyethyl)pyrrolidinium p-toluenesulfonate prepared in Reference Example 7, 0.1 ml of phosphorus oxychloride, 0.3 ml of triethylamine, 6 ml of chloroform having passed through an alumina column, and 8 ml of dry pyridine, to give 310 mg of the desired compound.

$^1$H NMR (CD$_3$OD) δ: 0.90 (t, 3H), 1.28 (s, 26H), 1.3–4.1 (m, 26H), 4.68 (s, 2H), 7.1–7.4 (m, 5H).

IR (KBr) cm$^{-1}$: 3400, 2910, 2845, 1460, 1220, 1090, 1060, 950, 730.

EXAMPLE 16

2-Acetyloxy-3-hexadecyloxypropyl 2-(1,1-dimethylpyrrolidinio-2-yl)ethyl phosphate (1) The procedures of Example 8-(1) were repeated using 260 mg of 2-benzyloxy-3-hexadecyloxypropyl 2-(1,1-dimethylpyrrolidinio-2-yl)ethyl phosphate prepared in Example 15, 50 mg of palladium(5%)-carbon and 30 ml of ethanol, to give 220 mg of 3-hexadecyloxy-2-hydroxypropyl 2-(1,1-dimethylpyrrolidinio-2-yl)ethyl phosphate.

$^1$H NMR (CD$_3$OD) δ: 0.90 (t, 3H), 1.28 (s, 26H), 1.3–4.1 (m, 26H).

IR (KBr) cm$^{-1}$: 3400, 2925, 2850, 1470, 1220, 1060, 955, 880, 820, 720.

(2) The procedures of Example 8-(2) were repeated using 200 mg of 3-hexadecyloxy-2-hydroxypropyl 2-(1,1-dimethylpyrrolidinio-2-yl)ethyl phosphate obtained as above, 1 g of acetic anhydride, 400 mg of triethylamine, and 20 ml of chloroform to give 130 mg of the desired compound.

$^1$H NMR (CD$_3$OD) δ: 0.89 (t, 3H), 1.28 (s, 26H), 1.3–2.4 (m, 9H), 2.04 (s, 3H), 2.8–4.3 (m, 16H), 4.9–5.2 (m, 1H).

IR (KBr) cm$^{-1}$: 3400, 2910, 2840, 1730, 1460, 1370, 1230, 1090, 1060, 1020, 950, 810, 710.

EXAMPLE 17

2-Benzyloxy-3-hexadecyloxypropyl 1,1-dimethylpiperidinio-3-yl phosphate

The procedures of Example 1 were repeated using 407 mg of 2-benzyloxy-3-hexadecyloxy-1-propanol, 452 mg of 1,1-dimethyl-3-hydroxypiperidinium p-toluenesulfonate (prepared from 1-methyl-3-piperidinol and methyl p-toluenesulfonate), 0.12 ml of phosphorus oxychloride, 0.35 ml of triethylamine and 3 ml of chloroform to give 293 mg of the desired compound.

$^1$H NMR (CD$_3$OD) δ: 0.89 (t, 3H), 1.28 (s, 26H), 1.3–4.6 (m, 24H), 4.69 (s, 2H), 7.15–7.45 (m, 5H).

IR (KBr) cm$^{-1}$: 3400, 3060, 3025, 2920, 2850, 1460, 1220, 1080, 1055, 1020.

EXAMPLE 18

2-Benzyloxy-3-hexadecyloxypropyl 1,1-dimethylpiperidinio-4-yl phosphate

The procedures of Example 1 were repeated using 366 mg of 2-benzyloxy-3-hexadecyloxy-1-propanol, 407 mg of 1,1-dimethyl-4-hydroxypiperidinium p-toluenesulfonate (prepared from 1-methyl-4-piperidinol and methyl p-toluenesulfonate), 0.10 ml of phosphorus oxychloride, 0.31 ml of triethylamine, 7 ml of chloroform having passed through an alumina column, and 8 ml of dry pyridine except that the reaction with the p-toluenesulfonate was carried out under irradiation of ultrasonic wave, to give 109 mg of the desired compound.

$^1$H NMR (CD$_3$OD) δ: 0.89 (t, 3H), 1.28 (s, 26H), 1.3–4.5 (m, 24H), 4.69 (s, 2H), 7.1–7.4 (m, 5H).

IR (KBr) cm$^{-1}$: 3430, 3030, 2940, 2870, 1470, 1240, 1110, 1090, 1065, 1045, 1010, 930, 865.

EXAMPLE 19

2-Benzyloxy-3-hexadecyloxybutyl 1,1-dimethylpyrrolidinio-3-yl phosphate

The procedures of Example 1 were repeated using 419 mg of 2-benzyloxy-3-hexadecyloxy-1-butanol, 480 mg of 1,1-dimethyl-3-hydroxypyrrolidinium p-toluenesulfonate (prepared from 1-methyl-3-pyrrolidinol and methyl p-toluenesulfonate), 0.1 ml of phosphorus oxychloride, 0.3 ml of triethylamine, 7 ml of chloroform having passed through an alumina column, and 8 ml of dry pyridine, to give 150 mg of the desired compound.

$^1$H NMR (CD$_3$OD) δ: 0.89 (t, 3H), 1.18 (d, 3H), 1.28 (s, 26H), 1.3–2.6 (m, 4H), 2.95–4.1 (m, 17H), 4.68 (s, 2H), 7.1–7.4 (m, 5H).

IR (neat) cm$^{-1}$: 3450, 3010, 2910, 2850, 1460, 1370, 1240, 1090, 1060, 1020, 940, 920, 880, 800, 750.

EXAMPLE 20

2-Benzyloxy-3-hexadecyloxybutyl 1,1-dimethylpiperidinio-3-yl phosphate

The procedures of Example 1 were repeated using 631 mg of 2-benzyloxy-3-hexadecyloxy-1-butanol, 678 mg of 1,1-dimethyl-3-hydroxypiperidinium p-toluenesulfonate, 0.18 ml of phosphorus oxychloride, 0.52 ml of triethylamine, 9 ml of chloroform having passed through an alumina column, and 15 ml of dry pyridine, to give 527 mg of the desired compound.

$^1$H NMR (CD$_3$OD) δ: 0.89 (t, 3H), 1.18 (d, 3H), 1.28 (s, 26H), 1.3–4.6 (m, 23H), 4.71 (s, 2H), 7.1–7.6 (m, 5H).

IR (KBr) cm$^{-1}$: 3400, 2920, 2840, 1480, 1460, 1450, 1225, 1080, 1060, 1020, 965.

EXAMPLE 21

2-Benzyloxy-3-hexadecyloxybutyl 1,1-dimethylpiperidinio-4-yl phosphate

The procedures of Example 1 were repeated using 2,100 mg of 2-benzyloxy-3-hexadecyloxy-1-butanol, 2480 mg of 1,1-dimethyl-4-hydroxypiperidinium p-toluenesulfonate, 0.5 ml of phosphorus oxychloride, 1.5 ml of triethylamine, 30 ml of chloroform having passed through an alumina column, and 40 ml of dry pyridine, to give 420 mg of the desired compound.

$^1$H NMR (CD$_3$OD) δ: 0.90 (t, 3H), 1.0–1.2 (m, 3H), 1.28 (s, 26H), 1.3–4.5 (m, 23H), 4.70 (s, 2H), 7.2–7.5 (m, 5H).

IR (KBr) cm$^{-1}$: 3400, 2920, 2850, 1460, 1380, 1230, 1070, 1040, 1000, 920, 855, 740, 700, 660.

REFERENCE EXAMPLE 8

Erythro-1,1-dimethyl-2-(α-hydroxybenzyl)pyrrolidinium p-toluenesulfonate

In 20 ml of acetone was dissolved 2.16 g of erythro-1-methyl-2-(α-hydroxybenzyl)pyrrolidine, and 2.10 g of methyl p-toluenesulfonate was added dropwise to the resulting solution. The mixture was stirred at room temperature, heated under reflux, and cooled to precipitate crystals. The crystals were collected by filtration and dried to give 3.80 g of the desired compound, m.p. 155°–157° C.

$^1$H NMR (DMSO-d$_6$) δ: 1.5–2.2 (m, 4H), 2.28 (s, 3H), 3.12 (s, 3H), 3.20 (s, 3H), 3.3–3.85 (m, 3H), 5.2–5.35 (m, 1H), 6.09 (d, 1H), 6.9–7.5 (m, 9H).

IR (KBr) cm$^{-1}$: 3320, 3070, 3025, 3000, 2975, 2920, 1450, 1215, 1190, 1135, 1110, 1045, 1030, 1010, 820, 700, 690, 570.

EXAMPLE 22

2-Benzyloxy-3-hexadecyloxybutyl erythro-1,1-dimethylpyrrolidinio-2-ylphenylmethyl phosphate The procedures of Example 1 were repeated using 842 mg of 2-benzyloxy-3-hexadecyloxy-1-butanol, 1155 mg of erythro-1,1-dimethyl-2-(α-hydroxybenzyl)pyrrolidinium p-toluenesulfonate prepared in Reference Example 8, 0.20 ml of phosphorus oxychloride, 0.60 ml of triethylamine, 6 ml of chloroform having passed through an alumina column, and 16 ml of dry pyridine, to give 459 mg of the desired compound.

$^1$H NMR (CD$_3$OD) δ: 0.7–1.1 (m, 6H), 1.28 (s, 26H), 1.3–3.9 (m, 3H), 4.2–4.6 (m, 2H), 5.70 (d, 1H), 7.1–7.6 (m, 10H).

IR (KBr) cm$^{-1}$: 3420, 2920, 2850, 1470, 1455, 1235, 1080, 860, 740, 700.

EXAMPLE 23

2-Benzyloxy-3-hexadecyloxypropyl erythro-1,1-dimethylpyrrolidinio-2-ylphenylmethyl phosphate The procedures of Example 1 were repeated using 338 mg of 2-benzyloxy-3-hexadecyloxy-1-propanol, 480 mg of erythro-1,1-dimethyl-2-(α-hydroxybenzyl)pyrrolidinium p-toluenesulfonate prepared in Reference Example 8, 0.09 ml of phosphorus oxychloride, 0.26 ml of triethylamine, 7 ml of chloroform having passed through an alumina column, and 8 ml of dry pyridine, to give 150 mg of the desired compound.

$^1$H NMR (CD$_3$OD) δ: 0.89 (t, 3H), 1.28 (s, 26H), 1.3–3.9 (m, 22H), 4.46 (s, 2H), 5.70 (d, 1H), 7.1–7.6 (m, 10H).

IR (KBr) cm$^{-1}$: 3400, 2920, 2850, 1465, 1450, 1230, 1080, 1065, 860, 730, 695.

REFERENCE EXAMPLE 9

Threo-1,1-dimethyl-2-(α-hydroxybenzyl)pyrrolidinium p-toluenesulfonate

The procedures of Reference Example 8 were repeated using 0.94 g of threo-1-methyl-2-(α-hydroxybenzyl)pyrrolidine and 0.91 g of methyl p-toluenesulfonate to give 1.65 g of the desired compound, m.p. 167°–168° C.

$^1$H NMR (DMSO-d$_6$) δ: 1.1–2.2 (m, 4H), 2.28 (s, 3H), 3.11 (s, 3H), 3.38 (s, 3H), 3.3–4.1 (m, 3H), 4.85 (dd, 1H), 6.19 (d, 1H), 6.95–7.6 (m, 9H).

IR (KBr) cm$^{-1}$: 3550, 3470, 3400, 3220, 3070, 3040, 3000, 2950, 2925, 1480, 1220, 1200, 1140, 1055, 1020, 820, 705.

EXAMPLE 24

2-Benzyloxy-3-hexadecyloxypropyl threo-1,1-dimethylpyrrolidinio-2-ylphenylmethyl phosphate The procedures of Example 1 were repeated using 407 mg of 2-benzyloxy-3-hexadecyloxy-1-propanol, 566 mg of threo-1,1-dimethyl-2-(α-hydroxybenzyl)pyrrolidinium p-toluenesulfonate prepared in Reference Example 9, 0.12 ml of phosphorus oxychloride, 0.35 ml of triethylamine, 6 ml of chloroform having passed through an alumina column, and 10 ml of dry pyridine, to give 283 mg of the desired compound.

$^1$H NMR (CD$_3$OD) δ: 0.89 (t, 3H), 1.28 (s, 26H), 1.3–2.1 (m, 6H), 2.8–4.3 (m, 16H), 4.45 (d, 2H), 5.1–5.45 (m, 1H), 6.9–7.55 (m, 10H).

IR (KBr) cm$^{-1}$: 3400, 3060, 3030, 2920, 2850, 1465, 1450, 1240, 1100, 1075, 1060, 1040, 1005, 960, 840, 695.

EXAMPLE 25

2-Acetyloxy-3-hexadecyloxypropyl erythro-1,1-dimethylpyrrolidinio-2-ylphenylmethyl phosphate In 3 ml of chloroform having passed through alumina was dissolved 0.12 ml of phosphorus oxychloride and 0.35 ml of triethylamine under nitrogen atmosphere, and the obtained solution was stirred for a while at room temperature. To the solution was dropwise added under chilling 3 ml of a solution of 359 mg of 2-acetyloxy-3-hexadecyloxy-1-propanol in chloroform (treated as above). After the addition was complete, the mixture was stirred for 30 hours at room temperature, and to the mixture were added a solution of 566 mg of erythro-1,1-dimethyl-2-(α-hydroxybenzyl)pyrrolidinium p-toluenesulfonate (prepared in Reference Example 8) in 8 ml of dry pyridine. The mixture was stirred overnight at room temperature and to the mixture were added 560 mg of sodium hydrogencarbonate and 1.5 ml of water. The resulting mixture was then stirred for a while. The solvent was distilled off under reduced pressure. To the residue was added 15 ml of a mixture of toluene and methylene chloride (v/v=1/1), and insolubles were filtered off. The filtrate was concentrated under reduced pressure, and the resulting residue was dissolved in a mixture of tetrahydrofuran and water (v/v=95/5). The solution was passed through a column of ion-exchange resin (Amberlite MB-3), which was then eluted with the same mixture of tetrahydrofuran and water. The eluate was placed under reduced pressure to distill off the solvent. The residue was purified by column chromatography using silica gel (eluent: chloroform/methanol/water=80/20/2) to obtain 122 mg of the desired compound.

$^1$H NMR (CD$_3$OD) δ: 0.90 (t, 3H), 1.29 (s, 26H), 1.95 (s, 3H), 1.3–3.9 (m, 21H), 4.4–4.9 (m, 1H), 7.2–7.55 (m, 5H).

IR (KBr) cm$^{-1}$: 3400, 2920, 2850, 1735, 1465, 1450, 1370, 1240, 1090, 1080, 1065.

EXAMPLE 26

2-Acetyloxy-3-hexadecyloxypropyl threo-1,1-dimethylpyrrolidinio-2-ylphenylmethyl phosphate The procedures of Example 25 were repeated using 359 mg of 2-acetyloxy-3-hexadecyloxy-1-propanol, 566 mg of threo-1,1-dimethyl-2-(α-hydroxybenzyl)pyrrolidinium p-toluenesulfonate prepared in Reference Example 9, 0.12 ml of phosphorus oxychloride, 0.35 ml of triethylamine, 6 ml of chloroform having passed through an alumina column, and 10 ml of dry pyridine, to give 207 mg of the desired compound.

$^1$H NMR (CD$_3$OD) δ: 0.89 (t, 3H), 1.28 (s, 26H), 1.95 (s, 3H), 1.3–2.1 (m, 9H), 2.8–4.3 (m, 15H), 4.35–4.7 (m, 1H) 5.1–5.45 (m, 1H), 7.2–7.55 (m, 5H).

IR (KBr) cm$^{-1}$: 3400, 2920, 2850, 1735, 1465, 1450, 1370, 1240, 1090, 1075, 1040.

REFERENCE EXAMPLE 10

2,2-Dimethyl-3-hydroxymethyl-1,2,3,4-tetrahydroisoquinolinium p-toluenesulfonate In a sealed tube, a mixture of 1.80 g of 1,2,3,4-tetrahydro-3-isoquinolinemethanol, 1.69 g of 90% formic acid and 1.04 g of 35% formalin was heated at 140° C. for 16 hours. The reaction solution was cooled and then made alkaline by addition of 10% aqueous sodium solution. Subsequently, potassium carbonate was added to the solution and a precipitated oil was extracted with chloroform. The extract was dried over anhydrous sodium sulfate and placed under reduced pressure to remove the solvent. There was obtained 1.95 g of 2-methyl-1,2,3,4-tetrahydro-3-isoquinolinemethanol.

In 12 ml of acetone was dissolved 887 mg of 2-methyl-1,2,3,4-tetrahydro-3-isoquinolinemethanol, and 932 mg of methyl p-toluenesulfonate was added dropwise to the resulting solution. The mixture was stirred at room temperature for 3 hours to precipitate crystals. The crystals were collected by filtration, washed with acetone and dried under reduced pressure to give 1.31 g of the desired compound.

$^1$H NMR (CDCl$_6$) δ: 2.25 (s, 3H), 2.6–4.8 (m, 7H), 3.05 (s, 3H), 3.50 (s, 3H), 5.53 (t, 1H), 6.8–7.7 (m, 8H).

IR (KBr) cm$^{-1}$: 3310, 3240, 1460, 1235, 1210, 1195, 1130, 1045, 690, 570.

EXAMPLE 27

2-Acetyloxy-3-hexadecyloxypropyl 2,2-dimethyl-1,2,3,4-tetrahydroisoquinolinio-3-ylmethyl phosphate The procedures of Example 25 were repeated using 359 mg of 2-acetyloxy-3-hexadecyloxy-1-propanol, 545 mg of 2,2-dimethyl-3-hydroxymethyl-1,2,3,4-tetraisoquinolinium p-toluenesulfonate prepared in Reference Example 10, 0.12 ml of phosphorus oxychloride, 0.35 ml of triethylamine, 3 ml of chloroform having passed through an alumina column, and 10 ml of dry pyridine, to give 473 mg of the desired compound.

$^1$H NMR (CD$_3$OD) δ: 0.89 (t, 3H), 1.28 (s, 26H), 1.3–1.65 (m, 2H), 2.05 (s, 3H), 3.13 (s, 3H), 3.2–4.8 (m, 16H), 4.95–5.25 (m, 1H), 7.0–7.4 (m, 4H).

IR (KBr) cm$^{-1}$: 3400, 2920, 2850, 1735, 1460, 1370, 1240, 1100, 1080, 1060, 1030, 965, 850, 830, 745.

REFERENCE EXAMPLE 11

1,1-Dimethyl-2-hydroxymethyl-1,2,3,4-tetrahydroquinolinium p-toluenesulfonate

In 120 ml of ethanol, 6 g of methyl quinaldinate was reduced by hydrogen in the presence of 400 mg of platinum oxide to give 6.8 g of methyl 1,2,3,4-tetrahydroquinaldinate as an oil. 3.0 g of the resulting methylester was further reduced in a dry ether by 1 g of lithium aluminum hydride to give 2.6 g of 1,2,3,4-tetrahydro-2-quinolinemethanol. A mixture of 1.6 g of the resulting alcohol, 0.93 ml of dimethylsulfonic acid, 2.16 g of calcium carbonate and 8 ml of water was stirred at room temperature for 6 hours. To the reaction mixture was added ether and insolubles were removed by filtration. The organic portion was separated, washed with water and dried over anhydrous sodium sulfate. After removal of the solvent under reduced pressure, the organic portion was purified by silica gel column chromatography (eluent: chloroform) to give 1.4 g of 1-methyl-1,2,3,4-tetrahydro-2-quinolinemethanol as a pale yellow oil.

$^1$H NMR (CDCl$_6$) δ: 1.60 (br. s, 1H), 1.70–2.20 (m, 2H), 2.60–2.84 (m, 2H), 3.00 (s, 3H), 3.24–3.46 (m, 1H), 3.56–3.76 (m, 2H), 6.48–7.20 (m, 4H).

A mixture of 1.3 g of 1-methyl-1,2,3,4-tetrahydro-2-quinolinemethanol and 1.37 g of methyl p-toluenesulfonate was heated at 100° C. for 6 hours. The solvent was removed from the reaction mixture by decantation, and the residue was washed with ether to give 2.7 g of the desired compound as a dark red oil.

$^1$H NMR (CDCl$_6$) δ: 1.80–2.3 (m, 2H), 2.30 (s, 3H), 2.70–3.00 (m, 2H), 3.58 (s, 3H), 3.68 (s, 3H), 4.02 (s, 2H), 5.20 (br. s, 1H), 6.90–7.90 (m, 8H).

EXAMPLE 28

2-Benzyloxy-3-hexadecyloxypropyl 1,1-dimethyl-1,2,3,4-tetrahydroquinolinio-2-ylmethyl phosphate The procedures of Example 7 were repeated using 406 mg of 2-benzyloxy-3-hexadecyloxy-1-propanol, 580 mg of 1,1-dimethyl-1,2,3,4-tetrahydro-2-hydroxymethylquinolinium p-toluenesulfonate prepared in Reference Example 11, 0.1 ml of phosphorus oxychloride, 0.3 ml of triethylamine, 3 ml of chloroform having passed through an alumina column, and 8 ml of dry pyridine, to give 150 mg of the desired compound.

$^1$H NMR (CDCl$_3$) δ: 0.74–1.00 (m, 3H), 1.28 (s, 28H) 2.04–4.30 (m, 14H), 3.48 (s, 3H) 3.56 (s, 3H), 4.62 (s, 2H), 7.10–7.50 (m, 9H).

IR (KBr) cm$^{-1}$: 3400, 3030, 2905, 2840, 1490, 1450, 1230, 1090, 1060.

EXAMPLE 29

2-Acetyloxy-3-hexadecyloxypropyl 1,1-dimethyl-1,2,3,4-tetrahydroquinolinio-2-ylmethyl phosphate (1) In 80 ml of methanol, 1.2 g of 2-benzyloxy-3-hexadecyloxypropyl 1,1-dimethyl-1,2,3,4-tetrahydroquinolinio-2-ylmethyl phosphate was hydrogenated at room temperature and an atmospheric pressure in the presence of 300 mg of 10% palladium-carbon, to give 950 mg of 3-hexadecyloxy-2-hydroxypropyl 1,1-dimethyl-1,2,3,4-tetrahydroquinolinio-2-ylmethyl phosphate as a wax.

$^1$H NMR (CDCl$_3$) δ: 0.72–1.00 (m, 3H), 1.28 (s, 28H) 2.20–4.44 (m, 14H), 3.62 (s, 3H), 3.70 (s, 3H), 7.24–7.90 (m, 4H).

IR (KBr) cm$^{-1}$: 3400, 2905, 2840, 1480, 1460, 1230, 1090, 1070, 1050.

(2) The procedures of Example 8-(2) were repeated using 500 mg of 3-hexadecyloxy-2-hydroxypropyl 1,1-dimethyl-1,2,3,4-tetrahydroquinolinio-2-ylmethyl obtained as above, 2.5 g of acetic anhydride, 1 g of triethylamine, and 50 ml of chloroform to give 100 mg of the desired compound.

$^1$H NMR (CD$_3$OD) δ: 0.72–1.00 (m, 3H), 1.28 (s, 28H) 2.02 (s, 3H), 2.20–4.40 (m, 14H) 3.62 (s, 3H), 3.70 (s, 3H), 4.99–5.16 (m, 1H), 7.28–7.92 (m, 4H).

IR (KBr) cm$^{-1}$: 3400, 2915, 2845, 1730, 1460, 1370, 1235, 1090, 1070, 975, 820, 765, 540.

REFERENCE EXAMPLE 12

3,3-Dimethyl-4(R)-hydroxymethyl-1,3-thiazolidinium p-toluenesulfonate

The procedures of Reference Example 10 were repeated using 520 mg of 4(R)-hydroxymethyl-3-methyl-1,3-thiazolidine and 726 mg of methyl p-toluenesulfonate to give 1070 mg of the desired compound as a white crystalline product.

$^1$H NMR (DMSO-d$_6$) δ: 2.29 (s, 3H), 2.7–3.5 (m, 2H), 3.13 (s, 3H), 3.33 (s, 3H), 3.6–4.0 (m, 3H), 4.68 (s, 2H), 5.2–5.9 (br. s, 1H), 7.11 (d, 2H), 7.49 (d, 2H).

IR (KBr) cm$^{-1}$: 3380, 3240, 3005, 2960, 2850, 1470, 1460, 1215, 1190, 1135, 1050, 1015, 820, 700, 690, 570.

EXAMPLE 30

2-Acetyloxy-3-hexadecyloxypropyl 3,3-dimethyl-1,3-thiazolidinio-4-ylmethyl phosphate The procedures of Example 25 were repeated using 359 mg of 2-acetyloxy-3-hexadecyloxy-1-propanol, 479 mg of 3,3-dimethyl-4(R)-hydroxymethyl-1,3-thiazolidinium p-toluenesulfonate prepared in Reference Example 12, 0.12 ml of phosphorus oxychloride, 0.35 ml of triethylamine, 6 ml of chloroform having passed through an alumina column, and 10 ml of dry pyridine, to give 374 mg of the desired compound.

$^1$H NMR (CD$_3$OD) δ: 0.90 (m, 3H), 1.28 (s, 26H), 1.3–1.65 (m, 2H), 2.06 (s, 3H), 2.7–3.65 (m, 15H), 3.8–4.35 (m, 6H), 4.5–4.9 (m, 2H), 4.9–5.25 (m, 1H).

IR (KBr) cm$^{-1}$: 3400, 2925, 2855, 1740, 1470, 1380, 1245, 1100, 1080, 1060, 830.

REFERENCE EXAMPLE 13

1,1-Dimethyl-3-hydroxymethyl-1,2,5,6-tetrahydropyridinium p-toluenesulfonate

The procedures of Reference Example 10 were repeated using 2.8 g of 1-methyl-1,2,5,6-tetrahydro-3-pyridinemethanol and 4.1 g of methyl p-toluenesulfonate to give 6.19 g of the desired compound as a white crystalline product.

$^1$H NMR (CD$_3$OD) δ: 2.34 (s, 3H), 2.3–2.6 (m, 2H), 3.12 (s, 6H), 3.42 (t, 2H), 3.88 (br. s, 2H), 3.96 (br. s, 2H), 5.8–6.0 (m, 1H), 7.1–7.7 (m, 4H).

IR (neat) cm$^{-1}$: 3400, 3025, 2925, 1480, 1200, 1120, 1030, 1010, 970, 940, 820, 680.

EXAMPLE 31

2-Acetyloxy-3-hexadecyloxypropyl 1,1-dimethyl-1,2,5,6-tetrahydropyridinio-3-ylmethyl phosphate The procedures of Example 25 were repeated using 360 mg of 2-acetyloxy-3-hexadecyloxy-1-propanol, 940 mg of 1,1-dimethyl-3-hydroxymethyl-1,2,5,6-tetrahydropyridinium p-toluenesulfonate prepared in Reference Example 13, 0.1 ml of phosphorus oxychloride, 0.3 ml of triethylamine, 6 ml of chloroform having passed through an alumina column, and 8 ml of dry pyridine, to give 260 mg of the desired compound.

$^1$H NMR (CD$_3$OD) δ: 0.88 (t, 3H), 1.28 (s, 26H), 1.3–1.6 (m, 2H), 2.04 (s, 3H), 2.4–2.7 (m, 2H), 3.16 (s, 6H), 3.3–4.4 (m, 12H), 4.9–5.2 (m, 1H), 5.9–6.1 (m, 1H).

IR (KBr) cm$^{-1}$: 3400, 2910, 2850, 1730, 1460, 1370, 1240, 1090, 1060, 1010, 970, 940, 820, 720, 560, 510.

REFERENCE EXAMPLE 14

3,3-Dimethyl-4-hydroxymethyl-2-phenylthiazolidinium p-toluenesulfonate (1) 1.72 g of L-cysteine methylester hydrochloride was neutralized by addition of 0.84 g of sodium hydrogen carbonate. The resulting ester was dissolved in 2 ml of methanol, and to this solution was added a solution of 0.94 g of benzaldehyde in 3 ml of methanol. The mixture was then stirred at room temperature for 40 hours under a nitrogen atmosphere. Ether was added to the reaction mixture, and then the mixture was extracted with diluted hydrochloric acid. The extract was neutralized by addition of sodium hydrogen carbonate and then extracted with ether. The organic portion was dried over anhydrous sodium sulfate and placed under reduced pressure for distilling off the solvent. There was obtained 1.51 g of 4-methoxycarbonyl-2-phenylthiazolidine as a colorless oil.

$^1$H NMR (CD$_3$OD) δ: 2.9–4.1 (m, 2H), 3.76 (d, 3H), 4.3–4.5 (m, 1H), 5.46 and 5.62 (br. sx2, 1H), 7.2–7.6 (m, 5H).

(2) A solution of 2.23 g of 4-methoxycarbonyl-2-phenylthiazolidine in 20 m of acetonitrile was chilled to −15° C. and, after addition of 4.3 g of 35% formalin and 1.0 g of sodium cyanoborohydride, was stirred for 30 minutes. The mixture was made acidic by addition of acetic acid under chilling with ice and, after addition of water, was made alkaline by addition of potassium carbonate. The alkaline solution was extracted with ether, and the etheral extract was dried over anhydrous sodium sulfate. The extract was placed under reduced pressure to distill of the solvent. The residue was purified by silica gel column chromatography (eluent: chloroform) to give 2.37 g of 4-methoxycarbonyl-3-methyl-2-phenylthiazolidine as a colorless oil.

$^1$H NMR (CDCl$_3$) δ: 2.28 and 2.36 (sx2, 3H), 2.7–4.3 (m, 3H), 3.78 (s, 3H), 4.74 and 5.36 (sx2, 1H), 7.2–7.6 (m, 5H).

(3) A solution of 320 mg of sodium borohydride in 40 ml of ethanol was dropwise added to a solution of 680 mg of calcium chloride dihydrates in 20 ml of ethanol under chilling to −30° C. The resulting mixture was stirred at −30° C. for 30 minutes. To the mixture was added a solution of 2.37 g of 4-methoxycarbonyl-3-methyl-2-phenylthiazolidine in 10 ml of ethanol. The resulting mixture was stirred at 0° C. for 22 hours, and subsequently at room temperature for 1 hour. To the mixture was added 13 ml of 20% hydrochloric acid-ethanol solution. The resulting mixture was placed under reduced pressure to distill off the solvent. The residue was made alkaline by addition of 10 ml of conc. aqueous ammonia after addition of water. The aqueous mixture was extracted with methylene chloride. The extract was dried over anhydrous sodium sulfate and placed under reduced pressure to remove the solvent. The residue was purified by silica gel column chromatography (eluent: chloroform) to give 1.00 g of 4-hydroxymethyl-3-methyl-2-phenylthiazolidine.

$^1$H NMR (CDCl$_3$) δ: 2.16 and 2.24 (sx2, 3H), 2.3–2.5 (m, 1H), 2.6–3.5 (m, 3H), 3.5–4.0 (m, 2H), 4.74 and 5.54 (sx2, 1H), 7.2–7.6 (m, 5H).

(4) In 10 ml of acetone, 1.00 g of 4-hydroxymethyl-3-methyl-2-phenylthiazolidine and 0.89 g of methyl p-toluenesulfonate were heated under reflux for 52 hours. The mixture was then placed under reduced pressure to distill off the solvent, and ether was added to the residue. Insolubles were washed with ether and dried under reduced pressure to give 1.74 g of the desired compound.

$^1$H NMR (CD$_3$OD) δ: 2.36 (s, 3H), 2.86 and 2.92 (sx2, 3H), 3.16 and 3.22 (sx2, 3H) 2.5–4.5 (m, 5H), 6.07 and 6.13 (sx2, 1H), 7.1–7.8 (m, 9H).

IR (neat) cm$^{-1}$: 3300, 3050, 2960, 2920, 2860, 1445, 1215, 1170, 1120, 1025, 1000, 815, 675, 560.

EXAMPLE 32

2-Acetyloxy-3-hexadecyloxypropyl 3,3-dimethyl-2-phenyl-1,3-thiazolidinio-4-ylmethyl phosphate The procedures of Example 25 were repeated using 198 mg of 2-acetyloxy-3-hexadecyloxy-1-propanol, 320 mg of 3,3-dimethyl-4-hydroxymethyl-2-phenyl-thiazolidinium p-toluenesulfonate prepared in Reference Example 14, 0.05 ml of phosphorus oxychloride, 0.15 ml of triethylamine, 3 ml of chloroform having passed through an alumina column, and 4 ml of dry pyridine, to give 120 mg of Product A and 30 mg of Product B, which were two isomers of the desired compound and were separated from each other by TLC (thin layer chromatography).

Product A $^1$H NMR (CD$_3$OD) δ: 0.88 (t, 3H), 1.28 (s, 26H), 1.3–1.6 (m, 2H), 2.06 (s, 3H), 2.92 (s, 3H), 3.16 (s, 3H), 3.3–3.6 (m, 5H), 3.9–4.1 (m, 2H), 4.2–4.4 (m, 4H), 5.0–5.2 (m, 1H), 6.16 (s, 1H), 7.4–7.8 (m, 5H).

IR (KBr) cm$^{-1}$: 3375, 2910, 2850, 1730, 1450, 1370, 1240, 1060, 810, 750.

Product B $^1$H NMR (CD$_3$OD) δ: 0.88 (t, 3H), 1.28 (s, 26H), 1.3–1.6 (m, 2H), 2.04 (s, 3H), 2.96 (s, 3H), 3.26 (s, 3H), 3.3–3.7 (m, 5H), 3.9–4.1 (m, 2H), 4.2–4.4 (m, 4H), 5.0–5.2 (m, 1H), 6.08 (s, 1H), 7.4–7.8 (m, 5H).

IR (KBr) cm$^{-1}$: 3400, 2910, 2850, 1735, 1450, 1360, 1230, 1080.

REFERENCE EXAMPLE 15

3,4-Dimethyl-5-(2-hydroxyethyl)-thiazolium p-toluenesulfonate

The procedures of Reference Example 10 were repeated using 0.71 g of 5-(2-hydroxyethyl)-4-methyl-thiazole and 0.95 g of methyl p-toluenesulfonate to give 1.25 g of the desired compound.

$^1$H NMR (DMSO-d$_6$) δ: 2.34 (s, 3H), 2.46 (s, 3H), 3.05 (t, 2H), 4.13 (s, 3H), 4.7–5.3 (br., 1H), 7.0–7.6 (m, 4H), 9.96 (s, 1H).

IR (KBr) cm$^{-1}$: 3410, 1590, 1450, 1200, 1185, 1130, 1040, 1010, 815, 685, 570.

EXAMPLE 33

2-Acetyloxy-3-hexadecyloxypropyl 3,4-dimethylthiazolio-5-ylethyl phosphate

The procedures of Example 25 were repeated using 357 mg of 2-acetyloxy-3-hexadecyloxy-1-propanol, 492 mg of 3,4-dimethyl-5-(2-hydroxyethyl)-thiazolium p-toluenesulfonate prepared in Reference Example 15, 0.12 ml of phosphorus oxychloride, 0.35 ml of triethylamine, 6 ml of chloroform, and 8 ml of dry pyridine, to give 152 mg the desired compound.

$^1$H NMR (DMSO-d$_6$) δ: 0.85 (t, 3H), 1.23 (s, 26H), 1.3–1.6 (m, 2H), 1.99 (s, 3H), 2.44 (s, 3H), 3.0–4.1 (m, 13H) 4.91 (q, 1H), 10.00 (s, 1H).

IR (KBr) cm$^{-1}$: 3410, 2920, 2850, 1730, 1445, 1370, 1235, 1090, 1060, 830.

REFERENCE EXAMPLE 16

3-(β-Hydroxyethyl)-1-methylpyridinium p-toluenesulfonate

The procedures of Reference Example 10 were repeated using 1.00 g of 3-pyridinethanol and 1.51 g of methyl p-toluenesulfonate to give 2.51 g of the desired compound.

$^1$H NMR (DMSO-d$_6$) δ: 2.36 (s, 3H), 3.00 (t, 2H), 3.84 (t, 2H), 4.34 (s, 3H), 7.1–8.8 (m, 8H).

IR (KBr) cm$^{-1}$: 3400, 3050, 2925, 1500, 1300, 1210, 1180, 1120, 1030, 1000, 810, 670.

EXAMPLE 34

2-Acetyloxy-3-hexadecyloxypropyl 1-methylpyridinio-3-ylethyl phosphate

The procedures of Example 25 were repeated using 358 mg of 2-acetyloxy-3-hexadecyloxy-1-propanol, 930 mg of 3-(β-hydroxyethyl)-1-methylpyridinium p-toluenesulfonate prepared in Reference Example 16, 0.1 ml of phosphorus oxychloride, 0.3 ml of triethylamine, 6 ml of chloroform, and 8 ml of dry pyridine, to give 250 mg of the desired compound.

$^1$H NMR (CD$_3$OD) δ: 0.88 (t, 3H), 1.28 (s, 26H), 1.3–1.7 (m, 2H), 2.04 (s, 3H), 3.12 (t, 2H), 3.42 (t, 2H), 3.54 (d, 2H), 3.86 (t, 2H), 4.0–4.2 (m, 2H), 4.38 (s, 3H), 4.9–5.1 (m, 1H), 7.8–8.9 (m, 4H).

IR (KBr) cm$^{-1}$: 3400, 2900, 2840, 1730, 1500, 1460, 1370, 1230, 1090, 1060, 940, 810, 670.

REFERENCE EXAMPLE 17

1,1-Dimethyl-3-hydroxymethyl-4-phenylpiperidinium p-toluenesulfonate

The procedures of Reference Example 10 were repeated using 1.0 g of 1-methyl-4-phenyl-3-piperidinemethanol and 910 mg of methyl p-toluenesulfonate to give 900 mg of the desired compound.

$^1$H NMR (CD$_3$OD) δ: 1.90–2.80 (m, 4H), 2.36 (s, 3H), 3.10–3.90 (m, 12H), 7.10–7.76 (m, 4H).

EXAMPLE 35

2-Benzyloxy-3-hexadecyloxypropyl 1,1-dimethyl-4-phenylpiperidinio-3-ylmethyl phosphate The procedures of Example 7 were repeated using 406 mg of 2-benzyloxy-1-hexadecyloxypropanol, 620 mg of 1,1-dimethyl-3-hydroxymethyl-4-phenylpiperidinium p-toluenesulfonate prepared in Reference Example 17, 0.1 ml of phosphorus oxychloride, 0.3 ml of triethylamine, 6 ml of chloroform having passed through an alumina column, and 8 ml of dry pyridine, to give 500 mg of the desired compound.

$^1$H NMR (CD$_3$OD) δ: 0.72–1.04 (m, 3H), 1.10–1.68 (m, 28H), 1.80–2.80 (m, 4H), 3.24 (d, 6H), 3.20–3.90 (m, 9H), 4.58 (s, 2H), 7.10–7.40 (m, 15H).

IR (KBr) cm$^{-1}$: 3400, 3050, 2910, 2840, 1230, 1090, 1060, 835, 690.

EXAMPLE 36

2-Acetyloxy-3-hexadecyloxypropyl 1,1-dimethyl-4-phenylpiperidinio-3-ylmethyl phosphate (1) In 30 ml of methanol, 370 mg of 2-benzyloxy-3-hexadecyloxypropyl 1,1-dimethyl-4-phenylpiperidinio-3-ylmethyl phosphate was hydrogenated at room temperature and an atmospheric pressure in the presence of 100 mg of 10% palladium-carbon, to give 270 mg of 3-hexadecyloxy-2-hydroxypropyl 1,1-dimethyl-4-phenylpiperidinio-3-ylmethyl phosphate as a wax.

$^1$H NMR (CDCl$_3$) δ: 0.72–1.02 (m, 3H), 1.10–1.8 (m, 28H), 1.90–2.80 (m, 4H), 3.10–3.90 (m, 15H), 7.10–7.40 (m, 5H).

IR (KBr) cm$^{-1}$: 3400, 2910, 2840, 1220, 1090, 1060, 1030, 830, 750, 690.

(2) The procedures of Example 8-(2) were repeated using 240 mg of 3-hexadecyloxy-2-hydroxypropyl 1,1-dimethyl-4-phenylpiperidinio-2-ylmethyl obtained as above, 1.03 g of acetic anhydride, 410 mg of triethylamine, and 25 ml of chloroform to give 200 mg of the desired compound.

$^1$H NMR (CD$_3$OD) δ: 0.76–1.00 (m, 3H), 1.10–1.60 (m, 28H), 1.96 (s, 3H), 2.10–2.80 (m, 4H), 3.10–3.90 (m, 15H) 4.90–5.10 (m, 1H), 7.10–7.44 (m, 5H).

IR (KBr) cm$^{-1}$: 3410, 2920, 2850, 1735, 1460, 1370, 1240, 1075, 1065, 1035, 830, 755, 695, 535.

REFERENCE EXAMPLE 18

3,3-Dimethyl-4(R)-hydroxymethyl-2-(2-methyl)propyl-1,3-thiazolidinium p-toluenesulfonate (1) A solution of 3.43 g of L-cysteine methylester hydrochloride and 1.72 g of isovaleroaldehyde in 20 ml of methanol was stirred at room temperature for 5 days. To the reaction mixture was added 2.02 g of triethylamine. The resulting mixture was concentrated under reduced pressure, and extracted with ether after addition of 10 ml of water. The etheral extract was dried over anhydrous sodium sulfate and placed under reduced pressure to distilled off the solvent. There was obtained 3.15 g of methyl 2-(2-methyl)propyl-1,3-thiazolidine-4(R)-carboxylate as a colorless oil.

$^1$H NMR (CDCl$_3$) δ: 0.7–1.2 (m, 6H), 1.3–2.3 (m, 3H), 2.3–2.6 (br., 1H), 2.65–3.45 (m, 2H), 3.77 and 3.78 (sx2, 3H), 3.7–4.8 (m, 2H).

(2) To a solution of 2.03 g of methyl 2-(2-methyl)propyl-1,3-thiazolidine-4(R)-carboxylate in 30 m of acetonitrile were added 4 ml of 35% formalin and 1.0 g of sodium cyanoborohydride. The resulting mixrture was stirred at room temperature for 40 minutes. After addition of a small amount of acetic acid, the mixture was placed under reduced pressure to distill off the solvent. To the residue were added 1 ml of water and 20 g of potassium carbonate, and the resulting mixture was extracted with methylene chloride. The extract was dried over anhydrous sodium sulfate and placed under reduced pressure to distill of the solvent. The residue was purified by silica gel column chromatography (eluent: chloroform to chlorofom/methanol(100/1)) to give 1.41 g of methyl 3-methyl-2-(2-methyl)propyl-1,3-thiazolidine-4(R)-carboxylate.

$^1$H NMR (CDCl$_3$) δ: 0.8–1.2 (m, 6H), 1.2–2.0 (m, 3H), 2.33 and 2.38 (sx2, 3H), 3.0–3.4 (m, 2H), 3.75 and 3.77 (sx2, 3H), 3.5–4.7 (m, 2H).

(3) In the same manner as in Reference Example 14-(3), a mixture of 3.88 mg of calcium chloride dihydrates, 182 mg of sodium borohydride and 1247 mg of methyl 3-methyl-2-(2-methyl)propyl-1,3-thiazolidine-4(R)-carboxylate was stirred overnight at a temperature of lower than −10° C., to give 369 mg of 3-methyl-2-(2-methyl)propyl-1,3-thiazolidine-4(R)-methanol.

$^1$H NMR (CDCl$_3$) δ: 0.7–1.2 (m, 6H), 1.2–1.9 (m, 3H), 2.28 and 2.38 (sx2, 3H), 2.2–3.7 (m, 6H), 3.8–4.65 (m, 1H).

(4) The procedures of Reference Example 10 were repeated using 369 mg of 3-methyl-2-(2-methyl)propyl-1,3-thiazolidine-4(R)-methanol and 363 mg of methyl p-toluenesulfonate to give 600 mg of the desired compound.

$^1$H NMR (DMSO-d$_6$) δ: 0.8–1.2 (m, 6H), 1.2–2.1 (m, 3H), 2.28 (s, 3H), 2.7–3.6 (m, 8H), 3.7–4.2 (m, 3H), 4.7–5.1 (m, 1H), 6.9–7.55 (m, 4H).

IR (KBr) cm$^{-1}$: 3400, 3030, 2960, 2930, 2880, 1470, 1215, 1200, 1125, 1035, 1015, 820, 685, 580.

EXAMPLE 37

2-Acetyloxy-3-hexadecyloxypropyl 3,3-dimethyl-2-(2-methyl)propyl-1,3-thiazolidinio-4-ylmethyl phosphate The procedures of Example 25 were repeated using 300 mg of 2-acetyloxy-3-hexadecyloxy-1-propanol, 473 mg of 3,3-dimethyl-4(R)-hydroxymethyl-2-(2-methyl)-propyl-1,3-thiazolidinium p-toluenesulfonate prepared in Reference Example 18, 0.10 ml of phosphorus oxychloride, 0.29 ml of triethylamine, 5 ml of chloroform having passed through an alumina column, and 8 ml of dry pyridine, to give 253 mg of Product A and 85 mg of Product B, which were two isomers of the desired compound and were separated from each other by TLC.

Product A $^1$H NMR (CD$_3$OD) δ: 0.8–1.2 (m, 9H), 1.28 (s, 26H), 1.3–2.2 (m, 5H), 2.06 (s, 3H), 2.8–3.65 (m, 12H), 3.8–4.4 (m, 5H), 4.8–5.25 (m, 2H).

IR (KBr) cm$^{-1}$: 3400, 2950, 2925, 2850, 1735, 1465, 1370, 1240, 1190.

Product B

¹H NMR (CD₃OD) δ: 0.8–1.2 (m, 9H), 1.28 (s, 26H), 1.3–2.2 (m, 5H), 2.06 (s, 3H), 2.8–3.65 (m, 12H), 3.8–4.4 (m, 5H), 4.8–5.25 (m, 2H)
IR (KBr) cm⁻¹: 3400, 2950, 2925, 2850, 1740, 1470, 1375, 1240, 1190.

REFERENCE EXAMPLE 19

3-(3-Hydroxy-1-propenyl)-1-methylpyridinium p-toluenesulfonate

Ethyl 3-(3-pyridyl)acrylate was reduced using lithium aluminum hydride to give 3-(3-pyridyl)-2-propen-1-ol. In 30 ml of acetone 710 mg of 3-(3-pyridyl)-2-propen-1-ol and 980 mg of methyl p-toluenesulfonate were heated under reflux for 22 hours. The reaction mixture was subjected by decantation to remove the solvent and then washed with acetone and ether. The residue was dried under reduced pressure to give 1.3 g of the desired compound as an orange-colored oil.

¹H NMR (CD₃OD) δ: 2.34 (s, 3H), 4.28 (d, 2H), 4.34 (s, 3H), 6.7–6.8 (m, 2H), 7.1–8.9 (m, 8H).
IR (neat) cm⁻¹: 3350, 3050, 1700, 1500, 1440, 1360, 1290, 1210, 1180, 1115, 1030, 1000, 960, 815, 670.

EXAMPLE 38

2-Acetyloxy-3-hexadecyloxypropyl 3-(1-methylpyridinio-3-yl)-2-propenyl phosphate The procedures of Example 25 were repeated using 358 mg of 2-acetyloxy-3-hexadecyloxy-1-propanol, 960 mg of 3-(3-hydroxy-1-propenyl)-1-methylpyridinium p-toluenesulfonate prepared in Reference Example 19, 0.1 ml of phosphorus oxychloride, 0.3 ml of triethylamine, 6 ml of chloroform having passed through an alumina column, and 8 ml of dry pyridine, to give 160 mg of the desired compound.

¹H NMR (CD₃OD) δ: 0.88 (t, 3H), 1.28 (s, 26H), 1.3–1.6 (m, 2H), 2.02 (s, 3H), 3.42 (t, 2H), 3.76 (d, 2H), 3.96 (t, 2H), 4.40 (br., 3H), 4.5–4.7 (m, 2H), 4.9–5.2 (m, 2H), 6.80 (br. s, 2H), 7.7–9.0 (m, 4H)
IR (KBr) cm⁻¹: 3400, 2900, 2850, 1730, 1500, 1455, 1370, 1230, 1080, 1010, 960, 850, 820, 660.

REFERENCE EXAMPLE 20

1-(1-Fluorophenyl)-3-hydroxymethyl-2-methylisoquinolinium p-toluenesulfonate 1-(1-Fluorophenyl)-3-isoquinolinecarboxylic acid was converted into its ethylester and then reduced using lithium aluminum hydride to obtain 1-(1-fluorophenyl)-3-isoquinolinemethanol. 1.26 g of the obtained 1-(1-fluorophenyl)-3-isoquinolinemethanol was reacted with 930 mg of methyl p-toluenesulfonate in the same manner as in Reference Example 10 to give 1.6 g of the desired compound as a pale orange-colored solid.

¹H NMR (CD₃OD) δ: 2.32 (s, 3H), 4.18 (s, 3H), 5.10 (s, 2H), 7.0–8.7 (m, 14H).
IR (KBr) cm⁻¹: 3250, 1565, 1480, 1440, 1410, 1380, 1325, 1220, 1170, 1115, 1020, 1000, 920, 840, 810, 800, 770, 620, 560.

EXAMPLE 39

2-Acetyloxy-3-hexadecyloxypropyl 1-(1-fluorophenyl)-2-methylisoquinolinio-3-ylmethyl phosphate The procedures of Example 25 were repeated using 358 mg of 2-acetyloxy-3-hexadecyloxy-1-propanol, 1.1 g of 1-(1-fluorophenyl)-3-hydroxymethyl-2-methylisoquinolinium p-toluenesulfonate prepared in Reference Example 20, 0.1 ml of phosphorus oxychloride, 0.3 ml of triethylamine, 6 ml of chloroform having passed through an alumina column, and 8 ml of dry pyridine, to give 260 mg of the desired compound.

¹H NMR (CD₃OD) δ: 0.88 (t, 3H), 1.28 (s, 26H), 1.3–1.6 (m, 2H), 2.00 (d, 3H), 3.3–3.5 (m, 2H), 3.54 (d, 2H), 3.9–4.1 (m, 2H), 4.24 (s, 3H), 4.9–5.2 (m, 1H), 5.40 (d, 2H), 7.4–8.8 (m, 9H).
IR (KBr) cm⁻¹: 3400, 2900, 2840, 1730, 1560, 1480, 1440, 1400, 1360, 1330, 1230, 1080, 820, 800, 750.

REFERENCE EXAMPLE 21

2-Acetyloxy-3-hexadecyloxy-1-butanol (1) In 100 ml of dry dimethylformamide, 17.67 g of 3-hexadecyloxybutane-1,2-diol was treated with 2.36 g of 60% sodium hydride under chilling with ice. To the chilled mixture was added 6.77 g of benzyl chloride, and the resulting mixture was stirred at room temperature for 16 hours. The reaction mixture was recovered in a conventional manner and purified by silica gel column chromatography to give 4.33 g of 1-benzyloxy-3-hexadecyloxy-2-butanol.

¹H NMR (CDCl₃) δ: 0.88 (m, 3H), 1.0–1.25 (m, 3H), 1.26 (s, 26H), 1.3–1.7 (m, 2H), 2.3–2.7 (br., 1H), 3.1–3.8 (m, 6H), 4.55 (s, 2H), 7.32 (s, 5H).

(2) In chloroform, 4.33 g of 1-benzyloxy-3-hexadecyloxy-2-butanol, 26.34 g of acetic anhydride and 10.42 g of triethylamine were heated under reflux for 17 hours. The reaction mixture was treated in a conventional manner and purified by silica gel column chromatography to give 4.56 g of 2-acetyloxy-1-benzyloxy-3-hexadecyloxybutane.

¹H NMR (CDCl₃) δ: 0.88 (t, 3H), 1.0–1.2 (m, 3H), 1.26 (s, 26H), 1.3–1.6 (m, 2H), 2.07, 2.09 (sx2, 3H), 3.0–3.8 (m, 5H), 4.52 (s, 2H), 4.9–5.15 (m, 1H), 7.2–7.4 (m, 5H).

(3) In methanol, 4.53 g of 2-acetyloxy-1-benzyloxy-3-hexadecyloxybutane was hydrogenated at 40° C. and an atmospheric pressure in the presence of 450 mg of 10% palladium-carbon, to give 3.60 g of the desired compound as a wax.

¹H NMR (CDCl₃) δ: 0.88 (t, 3H), 1.0–1.25 (m, 3H), 1.26 (s, 26H), 1.3–1.65 (m, 2H), 2.11 (s, 3H), 2.15–2.6 (br., 1H) 3.2–3.9 (m, 5H), 4.6–5.0 (m, 1H).

EXAMPLE 40

2-Acetyloxy-3-hexadecyloxybutyl 1,1-dimethyl-1,2,5,6-tetrahydropyridinio-3-ylmethyl phosphate The procedures of Example 25 were repeated using 373 mg of 2-acetyloxy-3-hexadecyloxy-1-butanol, 470 mg of 1,1-dimethyl-3-hydroxymethyl-1,2,5,6-tetrahydropyridinium p-toluenesulfonate prepared in Reference Example 13, 0.12 ml of phosphorus oxychloride, 0.35 ml of triethylamine, 6 ml of chloroform having passed through an alumina column, and 10 ml of dry pyridine, to give 63 mg of the desired compound.

¹H NMR (CD₃OD) δ: 0.89 (t, 3H), 1.0–1.25 (m, 3H), 1.28 (s, 26H), 1.3–1.65 (m, 2H), 2.08 (s, 3H), 2.35–2.7 (m, 2H), 3.17 (s, 6H), 2.9–4.1 (m, 9H), 4.2–4.4 (m, 2H), 4.8–5.2 (m, 1H), 5.9–6.1 (m, 1H).
IR (KBr) cm⁻¹: 3400, 2960, 2925, 2850, 1735, 1465, 1455, 1375, 1240, 1100, 1080, 1070.

EXAMPLE 41

2-Acetyloxy-3-hexadecyloxybutyl 3,3-dimethyl-2-phenyl-1,3-thiazolidinio-4-ylmethyl phosphate The procedures of Example 25 were repeated using 550 mg of 2-acetyloxy-3-hexadecyloxy-1-butanol, 940 mg of 3,3-dimethyl-4-hydroxymethyl-2-phenyl-thiazolinium p-toluenesulfonate prepared in Reference Example 14, 0.15 ml of phosphorus oxychloride, 0.44 ml of triethylamine, 9 ml of chloroform having passed through an alumina column, and 8 ml of dry pyridine, to give 160 mg of Product A and 70 mg of Product B, which were isomers of the desired compound, and were separated from each other by TLC.

Product A
$^1$H NMR (CD$_3$OD) δ: 0.89 (t, 3H), 1.14 (d, 3H), 1.28 (s, 26H), 1.3–1.7 (m, 2H), 2.08 (s, 3H), 2.94 (s, 3H), 3.20 (s, 3H), 3.3–3.7 (m, 5H), 3.8–4.5 (m, 5H), 6.18 (s, 1H), 7.4–7.8 (m, 5H).

IR (neat) cm$^{-1}$: 3350, 2900, 2850, 1730, 1440, 1360, 1220, 1100, 970, 810, 730, 700.

Product B
$^1$H NMR (CD$_3$OD) δ: 0.89 (t, 3H), 1.14 (d, 3H), 1.28 (s, 26H), 1.3–1.7 (m, 2H), 2.06 (s, 3H), 2.98 (s, 3H), 3.28 (s, 3H), 3.3–3.9 (m, 5H), 3.9–4.5 (m, 5H), 4.9–5.1 (m, 1H), 7.4–7.8 (m, 5H).

IR (neat) cm$^{-1}$: 3300, 2900, 2850, 1730, 1450, 1370, 1240, 1090, 800, 740.

EXAMPLE 42

2-Acetyloxy-3-hexadecyloxybutyl 3,4-dimethylthiazolio-5-ylethyl phosphate

The procedures of Example 25 were repeated using 745 mg of 2-acetyloxy-3-hexadecyloxy-1-butanol, 988 mg of 3,4-dimethyl-5-(2-hydroxyethyl)thiazolium p-toluenesulfonate prepared in Reference Example 15, 0.24 ml of phosphorus oxychloride, 0.70 ml of triethylamine, 12 ml of chloroform, and 20 ml of dry pyridine, to give 494 mg of the desired compound.

$^1$H NMR (CD$_3$OD) δ: 0.7–1.1 (m, 6H), 1.23 (s, 26H), 1.3–1.6 (m, 2H), 1.99 (s, 3H), 2.44 (s, 3H), 2.9–3.9 (m, 9H), 4.08 (s, 3H), 4.5–5.0 (m, 1H), 10.10 (s, 1H). (m, 1H), 5.9–6.1 (m, 1H)

IR (KBr) cm$^{-1}$: 3450, 2920, 2850, 1730, 1460, 1450, 1375, 1365, 1235, 1090, 1070, 1050, 825.

EXAMPLE OF PREPARATION: PELLETS

| | |
|---|---|
| (1) Glycerol derivative of the invention | 1.0 g |
| (2) Lactose | 27.0 g |
| (3) Crystalline cellulose | 20.0 g |
| (4) Corn starch | 5.0 g |
| (5) Carboxymethylcellulose calcium | 5.0 g |
| (6) Hydroxypropylcellulose | 1.6 g |
| (7) Magnesium stearate | 0.4 g |

A mixture of the components (1) to (6) was processed in the conventional manner to prepare granules, and the granules were then mixed with the component (7). The mixture was processed to form pellets (60 mg for one pellet which contained 1 mg of the component (1)).

EXAMPLE OF PREPARATION: INJECTIONS

In 10 liters of a distilled water for injection were dissolved 1.0 mg of a glycerol derivative of the invention 1.0 g and 100 g of mannitol. The solution was filtered under sterile condition, and the filtrate was divided into a plurality of 5 ml vials in an amount of 0.5 ml for one vial. The divided portions were freeze-dried in the conventional manner and then the vials were sealed tightly to give a freeze-dried agent for injection.

EXAMPLE OF PREPARATION: SOFT CAPSULES

| | |
|---|---|
| (1) Glycerol derivative of the invention | 0.1 g |
| (2) Polyethylene glycol 400 | 169.9 g |
| (3) Polyvinyl pyrrolidone | 5.0 g |
| (4) Glycerol | 75.0 g |

The components (1) to (4) was mixed to give a homogeneous solution. The solution was enclosed with gelatin sheets to give soft capsules containing 100 μg of the component (1) in one capsule.

We claim:
1. A glycerol derivative having the formula:

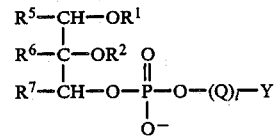

wherein
R$^1$ is a straight or branched chain alkyl group having 10–22 carbon atoms;

R$^2$ is a straight or branched chain acyl group having 1–6 carbon atoms or benzoyl;

R$^5$, R$^6$ and R$^7$ are independently hydrogen or a straight or branched chain alkyl group having 1–6 carbon atoms;

Q is a saturated or unsaturated alkylene divalent bridging radical having 1–4 carbon atoms optionally substituted by one or two methyl or phenyl groups, l is 1; and Y represents a heterocyclic group containing nitrogen and sulfur atoms selected from the group consisting of thiazolidinyl, thiazolyl, and benzothiazolyl, which has a moiety represented by

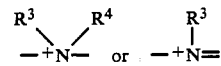

wherein R$^3$ and R$^4$ are independently a straight or branched chain alkyl group having 1–6 atoms, said heterocyclic group optionally having one or two substituents selected from the group consisting of a straight or branched chain alkyl group having 1–6 carbon atoms or phenyl, or a pharmaceutically acceptable salt thereof.

2. An anti-hypertensive composition useful in achieving reduction in blood pressure in the treatment of hypertension consisting of an effective amount of a glycerol compound in admixture with an inert carrier or diluent, wherein said compound has the formula:

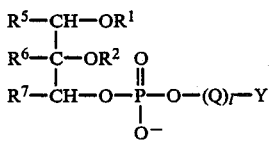

wherein
- $R^1$ is a straight or branched chain alkyl group having 10–22 carbon atoms;
- $R^2$ is a straight or branched chain acyl group having 1–6 carbon atoms or benzoyl;
- $R^5$, $R^6$ and $R^7$ are independently hydrogen or a straight or branched chain alkyl group having 1–6 carbon atoms;
- Q is a saturated or unsaturated alkylene divalent bridging radical having 1–4 carbon atoms optionally substituted by one or two methyl or phenyl groups,
- l is 1; and
- Y represents a heterocyclic group containing nitrogen and sulfur atoms selected from the group consisting of thiazolidinyl, thiazolyl, and benzothiazolyl, which has a moiety represented by

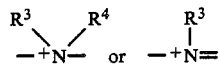

wherein $R^3$ and $R^4$ are independently a straight or branched chain alkyl group having 1–6 atoms, said heterocyclic group optionally having one or two substituents selected from the group consisting of a straight or branched chain alkyl group having 1–6 carbon atoms or phenyl, or a pharmaceutically acceptable salt thereof.

3. The glycerol derivative as claimed in claim 1, wherein $R^2$ is a straight chain acyl group having 2–6 carbon atoms.

4. The glycerol derivative as claimed in claim 1, wherein each of $R^5$, $R^6$ and $R^7$ is hydrogen.

5. A glycerol derivative as claimed in claim 1, wherein each of $R^5$ is a straight or branched chain alkyl group having 1–6 carbon atoms, and each of $R^6$ and $R^7$ is hydrogen.

6. The glycerol derivative as claimed in claim 1 which is 2-Acetyloxy-3-hexadecyloxypropyl 3,4-dimethylthiazolio-5-ylethyl phosphate.

7. An anti-hypertensive composition as claimed in claim 2 wherein the active compound is 2-Acetyloxy-3-hexadecyloxypropyl 3,4-dimethylthiazolio-5-ylethyl phosphate.

* * * * *